(12) United States Patent
Miller et al.

(10) Patent No.: US 11,241,534 B2
(45) Date of Patent: *Feb. 8, 2022

(54) POWER MANAGEMENT TECHNIQUES FOR AN INFUSION PUMP SYSTEM

(71) Applicant: Bigfoot Biomedical, Inc., Milpitas, CA (US)

(72) Inventors: Steve Miller, Palo Alto, CA (US); Ken Mochel, San Jose, CA (US); David C. Rich, West Bloomfield, MI (US)

(73) Assignee: BIGFOOT BIOMEDICAL, INC., Milpitas, CA (US)

( * ) Notice: Subject to any disclaimer, the term of this patent is extended or adjusted under 35 U.S.C. 154(b) by 374 days.

This patent is subject to a terminal disclaimer.

(21) Appl. No.: 16/256,403

(22) Filed: Jan. 24, 2019

(65) Prior Publication Data
US 2019/0151539 A1    May 23, 2019

Related U.S. Application Data

(60) Continuation of application No. 15/228,654, filed on Aug. 4, 2016, now Pat. No. 10,226,575, which is a
(Continued)

(51) Int. Cl.
*A61M 5/172* (2006.01)
*A61M 5/14* (2006.01)
(Continued)

(52) U.S. Cl.
CPC .......... *A61M 5/172* (2013.01); *A61M 5/1413* (2013.01); *A61M 5/14244* (2013.01);
(Continued)

(58) Field of Classification Search
CPC ................ A61M 5/172; A61M 5/1413; A61M 5/14244; A61M 5/14566; A61M 5/16831;
(Continued)

(56) References Cited

U.S. PATENT DOCUMENTS 2,605,765 A    8/1952  Kollsman
3,886,938 A    6/1975  Szabo et al.
(Continued)

FOREIGN PATENT DOCUMENTS

CA    2543545    5/2005
DE    19627619   1/1998
(Continued)

OTHER PUBLICATIONS

Medtronic News Release, "Medtronic Receives FDA Approval for World's First Insulin Pump with Real-time Continuous Glucose Monitoring," Apr. 13, 2006, 3 pages.
(Continued)

*Primary Examiner* — Theodore J Stigell
(74) *Attorney, Agent, or Firm* — Hamre, Schumann, Mueller & Larson, P.C.

(57) ABSTRACT

Some embodiments of an infusion pump system can employ a number of power management techniques to avoid using substantially excessive power during operation of the pump drive system. Thus, the infusion pump system can draw upon the energy supply in an efficient manner that extends the useful life on the power supply. Furthermore, the infusion pump system can be configured estimate an amount of power remaining to operate the pump system without the requirement of directly detecting the remaining charge on power supply device (e.g., without detecting the remaining charge on a battery). As such, the infusion pump system can readily inform a user of a particular estimated amount of time remaining for medicine dispensing operations.

20 Claims, 22 Drawing Sheets

Related U.S. Application Data division of application No. 13/613,160, filed on Sep. 13, 2012, now Pat. No. 9,415,158, which is a division of application No. 11/852,019, filed on Sep. 7, 2007, now Pat. No. 8,287,514.

(51) Int. Cl.
*A61M 5/145* (2006.01)
*A61M 5/142* (2006.01)
*A61M 5/168* (2006.01)
A61M 5/315 (2006.01)
H02J 7/00 (2006.01)
H02J 7/34 (2006.01)

(52) U.S. Cl.
CPC .... *A61M 5/14566* (2013.01); *A61M 5/16831* (2013.01); *A61M 2005/1402* (2013.01); *A61M 2005/14268* (2013.01); *A61M 2005/16863* (2013.01); *A61M 2005/31518* (2013.01); *A61M 2205/18* (2013.01); *A61M 2205/276* (2013.01); *A61M 2205/3317* (2013.01); *A61M 2205/50* (2013.01); *A61M 2205/502* (2013.01); *A61M 2205/52* (2013.01); *A61M 2205/581* (2013.01); *A61M 2205/583* (2013.01); *A61M 2205/8206* (2013.01); *A61M 2205/8237* (2013.01); *A61M 2205/8262* (2013.01); *H02J 7/0047* (2013.01); *H02J 7/342* (2020.01)

(58) Field of Classification Search
CPC ........... A61M 2005/1402; A61M 2005/14268; A61M 2005/16863; A61M 2005/31518; H02J 7/342
See application file for complete search history.

(56) References Cited

U.S. PATENT DOCUMENTS

| | | |
|---|---|---|
| 4,077,405 A | 3/1978 | Haerten et al. |
| 4,231,368 A | 11/1980 | Becker |
| 4,265,241 A | 5/1981 | Portner et al. |
| 4,300,554 A | 11/1981 | Hessberg et al. |
| 4,313,439 A | 2/1982 | Babb et al. |
| 4,398,908 A | 8/1983 | Siposs |
| 4,435,173 A | 3/1984 | Siposs et al. |
| 4,443,218 A | 4/1984 | DeCant, Jr. et al. |
| 4,493,704 A | 1/1985 | Beard et al. |
| 4,529,401 A | 7/1985 | Leslie et al. |
| 4,850,817 A | 7/1989 | Nason et al. |
| 4,919,650 A | 4/1990 | Feingold et al. |
| 5,045,064 A | 9/1991 | Idriss |
| 5,088,981 A | 2/1992 | Howson et al. |
| 5,190,522 A | 3/1993 | Wojcicki et al. |
| 5,250,027 A | 10/1993 | Lewis et al. |
| 5,261,882 A | 11/1993 | Sealfon et al. |
| 5,314,412 A | 5/1994 | Rex |
| 5,335,994 A | 8/1994 | Weynant Nee Girones |
| 5,338,157 A | 8/1994 | Blomquist |
| 5,342,180 A | 8/1994 | Daoud |
| 5,395,340 A | 3/1995 | Lee |
| 5,411,487 A | 5/1995 | Castagna |
| 5,545,143 A | 8/1996 | Fischell et al. |
| 5,551,850 A | 9/1996 | Williamson et al. |
| 5,558,639 A | 9/1996 | Gangemi et al. |
| 5,569,186 A | 10/1996 | Lord et al. |
| 5,626,566 A | 5/1997 | Petersen et al. |
| 5,637,095 A | 6/1997 | Nason et al. |
| 5,665,065 A | 9/1997 | Colman et al. |
| 5,712,795 A | 1/1998 | Layman et al. |
| 5,717,308 A | 2/1998 | Nishitani et al. |
| 5,741,216 A | 4/1998 | Hemmingsen et al. |
| 5,772,635 A | 6/1998 | Dastur et al. |
| 5,816,306 A | 10/1998 | Giacomel |
| 5,852,803 A | 12/1998 | Ashby, III et al. |
| 5,919,167 A | 7/1999 | Mulhauser |
| 5,925,018 A | 7/1999 | Ungerstedt |
| 5,928,201 A | 7/1999 | Poulsen et al. |
| 5,947,934 A | 9/1999 | Hansen et al. |
| 5,951,530 A | 9/1999 | Steengaard et al. |
| 5,957,889 A | 9/1999 | Poulsen et al. |
| 5,984,894 A | 11/1999 | Poulsen et al. |
| 5,984,897 A | 11/1999 | Petersen et al. |
| 5,997,475 A | 12/1999 | Bortz |
| 6,003,736 A | 12/1999 | Ljunggren |
| 6,010,485 A | 1/2000 | Buch-Rasmussen et al. |
| 6,033,377 A | 3/2000 | Rasmussen et al. |
| 6,045,537 A | 4/2000 | Klitmose |
| 6,074,372 A | 6/2000 | Hansen |
| 6,110,149 A | 8/2000 | Klitgaard et al. |
| 6,156,014 A | 12/2000 | Petersen et al. |
| 6,171,276 B1 | 1/2001 | Lippe et al. |
| 6,231,540 B1 | 5/2001 | Smedegaard |
| 6,248,067 B1 | 6/2001 | Causey, III et al. |
| 6,248,090 B1 | 6/2001 | Jensen et al. |
| 6,248,093 B1 | 6/2001 | Moberg |
| 6,277,098 B1 | 8/2001 | Klitmose et al. |
| 6,302,855 B1 | 10/2001 | Lav et al. |
| 6,302,869 B1 | 10/2001 | Klitgaard |
| 6,375,638 B2 | 4/2002 | Nason et al. |
| 6,379,339 B1 | 4/2002 | Klitgaard et al. |
| 6,381,496 B1 | 4/2002 | Meadows et al. |
| 6,404,098 B1 | 6/2002 | Kayama et al. |
| 6,427,088 B1 | 7/2002 | Bowman, IV et al. |
| 6,461,331 B1 | 10/2002 | Van Antwerp |
| 6,474,219 B2 | 11/2002 | Klitmose et al. |
| 6,485,461 B1 | 11/2002 | Mason et al. |
| 6,508,788 B2 | 1/2003 | Preuthun |
| 6,524,280 B2 | 2/2003 | Hansen et al. |
| 6,533,183 B2 | 3/2003 | Aasmul et al. |
| 6,537,251 B2 | 3/2003 | Klitmose |
| 6,540,672 B1 | 4/2003 | Simonsen et al. |
| 6,544,229 B1 | 4/2003 | Danby et al. |
| 6,547,764 B2 | 4/2003 | Larsen et al. |
| 6,551,276 B1 | 4/2003 | Mann et al. |
| 6,554,798 B1 | 4/2003 | Mann et al. |
| 6,554,800 B1 | 4/2003 | Nezhadian et al. |
| 6,558,320 B1 | 5/2003 | Causey, III et al. |
| 6,558,351 B1 | 5/2003 | Steil et al. |
| 6,562,001 B2 | 5/2003 | Lebel et al. |
| 6,562,011 B1 | 5/2003 | Buch-Rasmussen et al. |
| 6,564,105 B2 | 5/2003 | Starkweather et al. |
| 6,569,126 B1 | 5/2003 | Poulsen et al. |
| 6,571,128 B2 | 5/2003 | Lebel et al. |
| 6,577,899 B2 | 6/2003 | Lebel et al. |
| 6,582,404 B1 | 6/2003 | Klitgaard et al. |
| 6,585,644 B2 | 7/2003 | Lebel et al. |
| 6,585,699 B2 | 7/2003 | Ljunggreen et al. |
| 6,595,756 B2 | 7/2003 | Gray et al. |
| 6,605,067 B1 | 8/2003 | Larsen |
| 6,613,019 B2 | 9/2003 | Munk |
| 6,641,533 B2 | 11/2003 | Causey, III et al. |
| 6,648,821 B2 | 11/2003 | Lebel et al. |
| 6,650,951 B1 | 11/2003 | Jones et al. |
| 6,656,158 B2 | 12/2003 | Mahoney et al. |
| 6,656,159 B2 | 12/2003 | Flaherty |
| 6,659,948 B2 | 12/2003 | Lebel et al. |
| 6,659,978 B1 | 12/2003 | Kasuga et al. |
| 6,659,980 B2 | 12/2003 | Moberg et al. |
| 6,663,602 B2 | 12/2003 | Møller |
| 6,668,196 B1 | 12/2003 | Villegas et al. |
| 6,669,669 B2 | 12/2003 | Flaherty et al. |
| 6,687,546 B2 | 2/2004 | Lebel et al. |
| 6,691,043 B2 | 2/2004 | Ribeiro, Jr. |
| 6,692,457 B2 | 2/2004 | Flaherty |
| 6,692,472 B2 | 2/2004 | Hansen et al. |
| 6,694,191 B2 | 2/2004 | Starkweather et al. |
| 6,699,218 B2 | 3/2004 | Flaherty et al. |
| 6,702,779 B2 | 3/2004 | Connelly et al. |
| 6,715,516 B2 | 4/2004 | Ohms et al. |
| 6,716,198 B2 | 4/2004 | Larsen |
| 6,723,072 B2 | 4/2004 | Flaherty et al. |
| 6,733,446 B2 | 5/2004 | Lebel et al. |
| 6,736,796 B2 | 5/2004 | Shekalim |

(56) References Cited

U.S. PATENT DOCUMENTS

| | | |
|---|---|---|
| 6,740,059 B2 | 5/2004 | Flaherty |
| 6,740,072 B2 | 5/2004 | Starkweather et al. |
| 6,740,075 B2 | 5/2004 | Lebel et al. |
| 6,744,350 B2 | 6/2004 | Blomquist |
| 6,749,587 B2 | 6/2004 | Flaherty |
| 6,752,787 B1 | 6/2004 | Causey, III et al. |
| 6,758,810 B2 | 7/2004 | Lebel et al. |
| 6,768,425 B2 | 7/2004 | Flaherty et al. |
| 6,780,156 B2 | 8/2004 | Haueter et al. |
| 6,786,246 B2 | 9/2004 | Ohms et al. |
| 6,786,890 B2 | 9/2004 | Preuthun et al. |
| 6,796,970 B1 | 9/2004 | Klitmose et al. |
| 6,799,149 B2 | 9/2004 | Hartlaub |
| 6,809,653 B1 | 10/2004 | Mann et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,813,519 B2 | 11/2004 | Lebel et al. |
| 6,827,702 B2 | 12/2004 | Lebel et al. |
| 6,830,558 B2 | 12/2004 | Flaherty et al. |
| 6,852,104 B2 | 2/2005 | Blomquist |
| 6,854,620 B2 | 2/2005 | Ramey |
| 6,854,653 B2 | 2/2005 | Eilersen |
| 6,855,129 B2 | 2/2005 | Jensen et al. |
| 6,872,200 B2 | 3/2005 | Mann et al. |
| 6,873,268 B2 | 3/2005 | Lebel et al. |
| 6,878,132 B2 | 4/2005 | Kipfer |
| 6,893,415 B2 | 5/2005 | Madsen et al. |
| 6,899,695 B2 | 5/2005 | Herrera |
| 6,899,699 B2 | 5/2005 | Enggaard |
| 6,922,590 B1 | 7/2005 | Whitehurst |
| 6,936,006 B2 | 8/2005 | Sabra |
| 6,936,029 B2 | 8/2005 | Mann et al. |
| 6,945,961 B2 | 9/2005 | Miller et al. |
| 6,948,918 B2 | 9/2005 | Hansen |
| 6,950,708 B2 | 9/2005 | Bowman, IV et al. |
| 6,958,705 B2 | 10/2005 | Lebel et al. |
| 6,960,192 B1 | 11/2005 | Flaherty et al. |
| 6,979,326 B2 | 12/2005 | Mann et al. |
| 6,997,911 B2 | 2/2006 | Klitmose |
| 6,997,920 B2 | 2/2006 | Mann et al. |
| 7,005,078 B2 | 2/2006 | Van Lintel et al. |
| 7,008,399 B2 | 3/2006 | Larson et al. |
| 7,014,625 B2 | 3/2006 | Bengtsson |
| 7,018,360 B2 | 3/2006 | Flaherty et al. |
| 7,025,743 B2 | 4/2006 | Mann |
| 7,029,455 B2 | 4/2006 | Flaherty |
| 7,054,836 B2 | 5/2006 | Christensen et al. |
| 7,104,972 B2 | 9/2006 | Møller et al. |
| 7,128,727 B2 | 10/2006 | Flaherty et al. |
| 7,133,329 B2 | 11/2006 | Skyggebjerg et al. |
| 7,232,423 B2 | 6/2007 | Mernoe |
| 7,935,105 B2 | 5/2011 | Miller et al. |
| 8,211,093 B2 | 6/2012 | Miller et al. |
| 8,287,514 B2* | 10/2012 | Miller ............... A61M 5/172 604/500 |
| 8,523,803 B1 | 9/2013 | Favreau |
| 9,415,158 B2* | 8/2016 | Miller ............... A61M 5/14566 |
| 10,226,575 B2* | 3/2019 | Miller ............... A61M 5/14244 |
| 2001/0056262 A1 | 12/2001 | Cabiri |
| 2002/0004651 A1 | 1/2002 | Ljndggreen et al. |
| 2002/0007154 A1 | 1/2002 | Hansen et al. |
| 2002/0040208 A1 | 4/2002 | Flaherty et al. |
| 2002/0091358 A1 | 7/2002 | Klitmose |
| 2002/0126036 A1 | 9/2002 | Flaherty et al. |
| 2003/0055380 A1 | 3/2003 | Flaherty |
| 2003/0065308 A1 | 4/2003 | Lebel et al. |
| 2003/0088238 A1 | 5/2003 | Poulsen |
| 2003/0199825 A1 | 10/2003 | Flaherty |
| 2003/0199855 A1* | 10/2003 | Rogers ............... A61M 5/172 604/891.1 |
| 2003/0216683 A1 | 11/2003 | Shekalim |
| 2004/0010207 A1 | 1/2004 | Flaherty et al. |
| 2004/0019325 A1 | 1/2004 | Shekalim |
| 2004/0064088 A1 | 4/2004 | Gorman et al. |
| 2004/0064096 A1 | 4/2004 | Flaherty et al. |
| 2004/0078028 A1 | 4/2004 | Flaherty et al. |
| 2004/0087894 A1 | 5/2004 | Flaherty |
| 2004/0092865 A1 | 5/2004 | Flaherty et al. |
| 2004/0092878 A1 | 5/2004 | Flaherty |
| 2004/0116866 A1 | 6/2004 | Gorman et al. |
| 2004/0127844 A1 | 7/2004 | Flaherty |
| 2004/0153032 A1 | 8/2004 | Garribotto et al. |
| 2004/0171983 A1 | 9/2004 | Sparks et al. |
| 2004/0176727 A1 | 9/2004 | Shekalim |
| 2004/0204673 A1 | 10/2004 | Flaherty |
| 2004/0220551 A1 | 11/2004 | Flaherty et al. |
| 2004/0235446 A1 | 11/2004 | Flaherty et al. |
| 2004/0260233 A1 | 12/2004 | Garibotto et al. |
| 2005/0021005 A1 | 1/2005 | Flaherty et al. |
| 2005/0022274 A1 | 1/2005 | Campbell et al. |
| 2005/0065760 A1 | 3/2005 | Murtfeldt et al. |
| 2005/0086410 A1 | 4/2005 | Landron et al. |
| 2005/0090808 A1 | 4/2005 | Malave et al. |
| 2005/0095063 A1 | 5/2005 | Fathallah |
| 2005/0160858 A1 | 7/2005 | Mernoe |
| 2005/0171512 A1 | 8/2005 | Flaherty |
| 2005/0182366 A1 | 8/2005 | Vogt et al. |
| 2005/0192561 A1 | 9/2005 | Mernoe |
| 2005/0203461 A1 | 9/2005 | Flaherty et al. |
| 2005/0215982 A1 | 9/2005 | Malave et al. |
| 2005/0222645 A1 | 10/2005 | Malave et al. |
| 2005/0238507 A1 | 10/2005 | Dilanni et al. |
| 2005/0245878 A1 | 11/2005 | Mernoe et al. |
| 2005/0251097 A1 | 11/2005 | Mernoe |
| 2005/0267402 A1 | 12/2005 | Stewart et al. |
| 2005/0273059 A1 | 12/2005 | Mernoe et al. |
| 2006/0041229 A1 | 2/2006 | Garibotto et al. |
| 2006/0047367 A1 | 3/2006 | Rogers et al. |
| 2006/0069382 A1 | 3/2006 | Pedersen |
| 2006/0074381 A1 | 4/2006 | Malave et al. |
| 2006/0095014 A1 | 5/2006 | Ethelfeld |
| 2006/0135913 A1 | 6/2006 | Ethelfeld |
| 2006/0142698 A1 | 6/2006 | Ethelfeld |
| 2006/0178633 A1 | 8/2006 | Garibotto et al. |
| 2006/0184119 A1 | 8/2006 | Remde et al. |
| 2006/0200073 A1 | 9/2006 | Radmer et al. |
| 2006/0206054 A1 | 9/2006 | Shekalim |
| 2006/0247581 A1 | 11/2006 | Pedersen et al. |
| 2007/0073228 A1 | 3/2007 | Mernoe et al. |
| 2007/0073236 A1 | 3/2007 | Mernoe et al. |
| 2007/0124002 A1 | 5/2007 | Estes et al. |
| 2007/0156092 A1 | 7/2007 | Estes et al. |
| 2007/0167905 A1 | 7/2007 | Estes et al. |
| 2007/0167912 A1 | 7/2007 | Causey et al. |
| 2008/0125701 A1 | 5/2008 | Moberg et al. |
| 2008/0243079 A1 | 10/2008 | Wooley et al. |

FOREIGN PATENT DOCUMENTS

| | | |
|---|---|---|
| DE | 10236669 | 2/2004 |
| EP | 0496141 | 7/1992 |
| EP | 0612004 | 8/1994 |
| EP | 0580723 | 10/1995 |
| EP | 0275213 | 7/1998 |
| EP | 1045146 | 10/2000 |
| EP | 1136698 | 9/2001 |
| EP | 1177802 | 2/2002 |
| EP | 0721358 | 5/2002 |
| EP | 1495775 | 1/2005 |
| EP | 1527792 | 5/2005 |
| EP | 1754498 | 2/2007 |
| FR | 2585252 | 1/1987 |
| GB | 747701 | 4/1956 |
| GB | 2218831 | 11/1989 |
| WO | WO 1990/015928 | 12/1990 |
| WO | WO 1997/021457 | 6/1997 |
| WO | WO 1998/011927 | 3/1998 |
| WO | WO 1998/057683 | 12/1998 |
| WO | WO 1999/021596 | 5/1999 |
| WO | WO 1999/039118 | 8/1999 |
| WO | WO 1999/048546 | 9/1999 |
| WO | WO 2001/023277 | 4/2001 |
| WO | WO 2001/072360 | 10/2001 |

(56) References Cited

FOREIGN PATENT DOCUMENTS

| WO | WO 2001/091822 | 12/2001 |
|---|---|---|
| WO | WO 2001/091833 | 12/2001 |
| WO | WO 2002/040083 | 5/2002 |
| WO | WO 2002/057627 | 7/2002 |
| WO | WO 2002/100469 | 12/2002 |
| WO | WO 2003/103763 | 12/2003 |
| WO | WO 2004/056412 | 7/2004 |
| WO | WO 2004/110526 | 12/2004 |
| WO | WO 2005/002652 | 1/2005 |
| WO | WO 2005/039673 | 5/2005 |
| WO | WO 2005/072794 | 8/2005 |
| WO | WO 2005/072795 | 8/2005 |
| WO | WO 2006/105792 | 10/2006 |
| WO | WO 2006/105793 | 10/2006 |
| WO | WO 2006/105794 | 10/2006 |
| WO | WO 2007/145851 | 12/2007 |
| WO | WO 2007/145951 | 12/2007 |

OTHER PUBLICATIONS

Debiotech News Release, "Debiotech reveals its new miniaturized Disposable Insulin Nanopump™ for Diabetes therapy," available at http://www.debiotech.com/news/nw_159.html Apr. 24, 2006, 3 pages.
Patent Abstracts of Japan, vol. 1999, No. 04, and JP 11 010036, Apr. 30, 1999 and Jan. 19, 1999, Toray Ind. Inc.
Invitation to Pay Fees, PCT/US2008/069642, dated Dec. 23, 2008, 11 pages.
International Search Report and Written Opinion in International Application No. PCT/US2008/069642, dated Apr. 14, 2009, 19 pages.
International Preliminary Report on Patentability for Application No. PCT/US2008/069642, dated Mar. 18, 2010, 21 pages.

* cited by examiner

POWER MANAGEMENT TECHNIQUES FOR AN INFUSION PUMP SYSTEM

CROSS-REFERENCE TO RELATED APPLICATION(S)

This application is a continuation of U.S. patent application Ser. No. 15/228,654, filed on Aug. 4, 2016, which is a divisional of U.S. patent application Ser. No. 13/613,160, filed Sep. 13, 2012 (now U.S. Pat. No. 9,415,158), which is a divisional of U.S. patent application Ser. No. 11/852,019, filed on Sep. 7, 2007 (now U.S. Pat. No. 8,287,514), the entire contents of which are hereby incorporated by reference.

TECHNICAL FIELD

This document relates to managing the power usage in an infusion pump system.

BACKGROUND

Pump devices are commonly used to deliver one or more fluids to a targeted individual. For example, a medical infusion pump device may be used to deliver a medicine to a patient as part of a medical treatment. The medicine that is delivered by the infusion pump device can depend on the condition of the patient and the desired treatment plan. For example, infusion pump devices have been used to deliver insulin to the vasculature of diabetes patients so as to regulate blood-glucose levels. In some circumstances, the infusion pump devices may operate on battery power to facilitate portability of the pump devices.

SUMMARY

Some embodiments of an infusion pump system can employ a number of power management techniques to avoid using substantially excessive power during operation of the pump drive system. Thus, the infusion pump system can draw upon the energy supply in an efficient manner that extends the useful life on the power supply. Furthermore, the infusion pump system can be configured estimate an amount of power remaining to operate the pump system without the requirement of directly detecting the remaining charge on power supply device (e.g., without detecting the remaining charge on a battery). As such, the infusion pump system can readily inform a user of a particular estimated amount of time remaining for medicine dispensing operations.

In particular embodiments, a wearable infusion pump system may include a pump device and a controller device. The pump device can include a drive system to dispense medicine from the pump device and can also include a non-rechargeable battery. The controller device can include a rechargeable energy source that outputs electrical energy to the drive system of the pump device. The rechargeable energy source may receive electrical energy from the non-rechargeable battery of the pump device to maintain the rechargeable energy source at a charge level greater than a threshold charge level when the non-rechargeable battery is in a non-depleted state. The controller device can output an alert indicative of a remaining power supply based at least partially on the threshold charge level when the non-rechargeable battery of the pump device is in a depleted state or disconnected from electrical communication with the rechargeable energy source.

In some embodiments, a medicinal fluid supply system may include a drive system to dispense a medicine from a portable infusion pump unit. The system can also include control circuitry to communicate electronic control signals to the drive system. Furthermore, the system may include a rechargeable power supply electrically connected to the control circuitry. The drive system can be powered by the electrical energy stored in the rechargeable power supply. The system may also include a replaceable battery electrically connected to the rechargeable power supply. The rechargeable power supply can receive electrical energy from replaceable battery to maintain the rechargeable power supply at a charge level greater than a threshold charge level when the replaceable battery is in a non-depleted state. The system may further include a user interface that outputs a user alert indicative of a remaining power supply based at least partially on the threshold charge level when the non-rechargeable battery device is in a depleted state or disconnected from the electrical connection with the rechargeable power supply.

In particular embodiments, a method of administering medicinal fluid to a patient can include supplying electrical energy from a rechargeable energy source to a drive system of a pump device to activate the drive system and dispense medicinal fluid from the pump device. The method can also include charging the rechargeable energy source with energy from a replaceable battery to maintain the rechargeable energy source at a charge level greater than a threshold charge level when the replaceable battery is in a non-depleted state. The method may further include outputting a user alert indicative of a remaining power supply based at least partially on the threshold charge level when the replaceable battery is in a depleted state or disconnected from electrical communication with the rechargeable energy source.

Some embodiments of a wearable infusion pump system may include a pump device having a drive system to dispense medicine from the pump device. The drive system can define an energy requirement profile to perform a medicine dispensing operation. The system may also include an energy storage source to deliver electrical energy to the drive system. The system may further include a controller device to initiate the medicine dispensing operation by supplying a pattern of voltage pulses from the energy storage source to the drive system. The pattern of voltage pulses can be correlated to the energy requirement profile of the drive system.

In particular embodiments, a method of administering medicinal fluid to a patient can include delivering a pattern of voltage pulses from an energy source to a drive system of a portable infusion pump device. The pattern of voltage pulses can be correlated to an energy requirement profile defined by the drive system. The method can also include actuating one or more components of the drive system in response to the delivery of the pattern of voltage pulses so as to dispense a medicinal fluid from the portable infusion pump device.

In other embodiments, a wearable infusion pump system may include a disposable and non-reusable pump device and a reusable controller device. The disposable and non-reusable pump device can define a space to receive a medicine cartridge and can include a drive system to dispense medicine from the pump device. The drive system can define an energy requirement profile to perform a medicine dispensing operation. The reusable controller device can include a pulse-width modulation controller and an energy storage source to deliver electrical energy to the drive system. The pulse-width modulation controller can provide a pattern of voltage pulses from the energy storage source to the drive system. The pattern of voltage pulses can be correlated to the energy requirement profile of the drive system.

Some embodiments of a wearable infusion pump system may include a pump device including a drive system to dispense medicine from the pump device. Also, the system may include an energy storage source to deliver electrical energy to the drive system. The system may further include a controller device to initiate the medicine dispensing operation by supplying a pattern of voltage pulses from the energy storage source to the drive system. The controller device can detect a voltage output level of the energy storage source and can adjust the frequency or duration of the voltage pulses based on the detected voltage output level.

In particular embodiments, a method of administering medicinal fluid to a patient may include detecting a voltage output of an energy source electrically connected to a drive system of a portable infusion pump system. The portable infusion pump device can include a medicine dispensed to a user when one or more components of the drive system are actuated. The portable infusion pump system may actuate one or more components of the drive system by supplying patterns of voltage pulses from the energy source to the drive system. The method may also include determining a pattern of voltage pulses to be supplied to the drive system based on the detected voltage output. The method may further include delivering the determined pattern of voltage pulses from the energy source to the drive system of a portable infusion pump device to actuate one or more components of the drive system to dispense a medicinal fluid from the portable infusion pump device.

Some or all of the embodiments described herein may provide one or more of the following advantages. First, some embodiments of the infusion pump system may include a configuration that reliably predicts an amount of battery life remaining after a first battery in the disposable pump device is depleted. The controller device can then inform a user of a particular estimate amount of medicine dispensing time remaining. By informing the user that she has an amount of medicine dispensing time remaining, the user can ensure that she is able to supply additional energy to the infusion pump system all of the reserve power is depleted.

Second, certain embodiments of an infusion pump system may include a configuration that can estimate an amount of power remaining in the device without having to directly detect the remaining charge on the battery. Operations that directly detect the remaining charge level of a battery can themselves consume significant energy. Accordingly, by avoiding a direct measurement of remaining charge, power can be conserved and result in a longer battery life.

Third, some embodiments of the infusion pump system can conserve energy by using a pulse-width modulation system to actuate the drive system of the pump device. The use of pulse-width modulation can allow the infusion pump system to avoid using more power than necessary to operate the drive system. For example, the controller can provide a pattern of voltage pulses to the drive system that average out to approximately equal an energy requirement profile for the drive system. The widths of the pulses can be adjusted as the voltage output of the battery changes and the charge level of the battery changes.

Fourth, the infusion pump system may include a reusable controller device that is removably attachable to a disposable single-use pump device to provide an electrical connection therebetween. In these circumstances, the infusion pump system can include an rechargeable energy source arranged in the reusable controller device and a disposable battery in the disposable single-use pump device such that the rechargeable energy source is not discarded with the single-use pump device, but the disposable battery in the disposable pump device can be used to recharge the rechargeable energy source and then discarded with the disposable pump device. Accordingly, the rechargeable energy source instrumentation can be employed in a cost-effective manner that permits reuse of the instrumentation with a series of different pump devices each including another source of recharging energy for the rechargeable energy source.

Fifth, some embodiments of the pump device may be attached to the controller device so that a user can readily monitor infusion pump operation by simply viewing the user interface connected to the pump device. In these circumstances, the user may activate and control the pump device without the requirement of locating and operating a separate monitoring module.

Sixth, some embodiments of the infusion pump system may be configured to be portable, wearable, and (in some circumstances) concealable. For example, a user can conveniently wear the infusion pump system on the user's skin under clothing or can carry the pump device in the user's pocket (or other portable location) while receiving the medicine dispensed from the pump device.

The details of one or more embodiments are set forth in the accompanying drawings and the description below. Other features, objects, and advantages will be apparent from the description and drawings, and from the claims.

DETAILED DESCRIPTION OF ILLUSTRATIVE EMBODIMENTS

Figure 1:
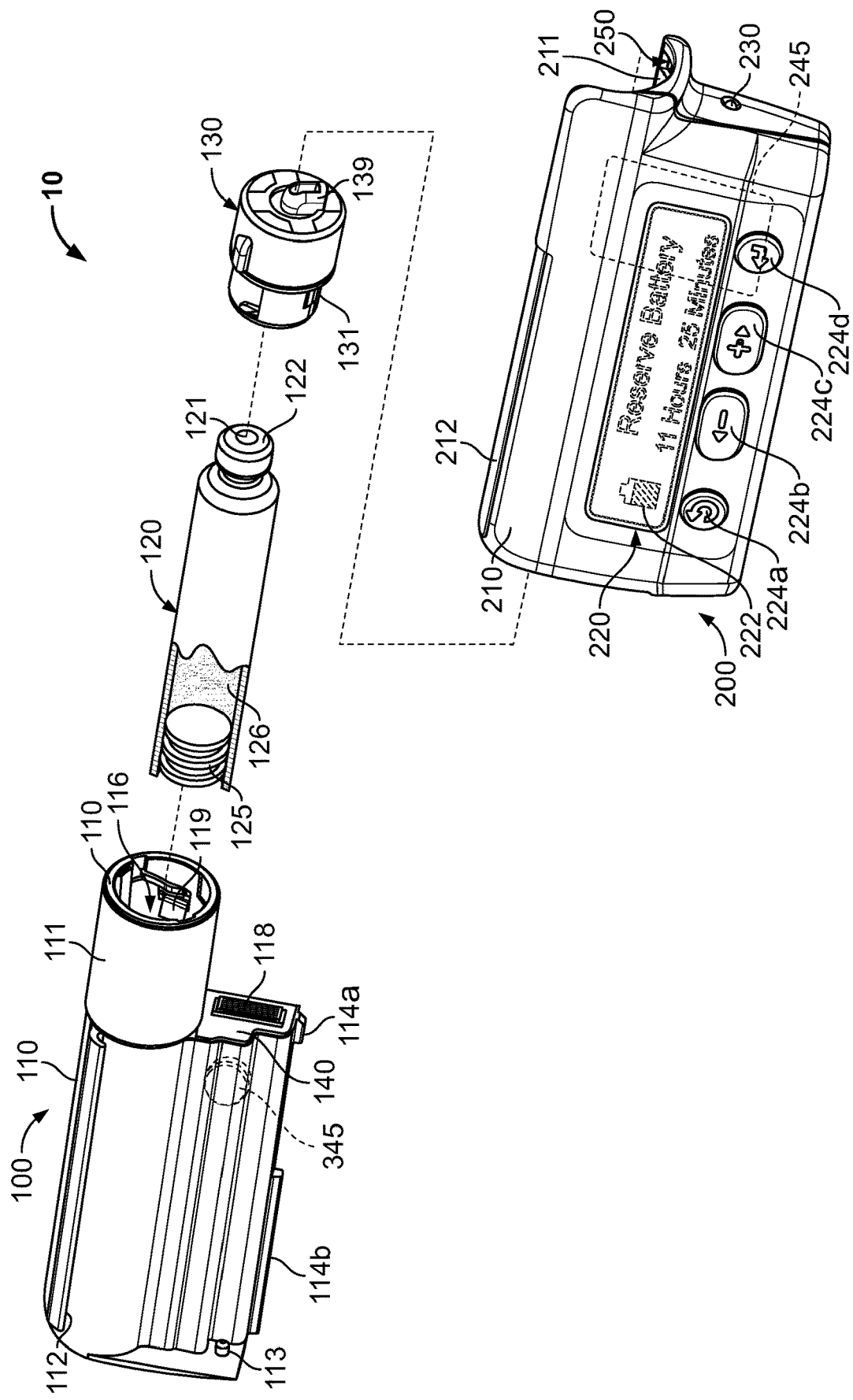
FIG. 1 is a perspective view of an infusion pump system in accordance with some embodiments.
Figure 2:
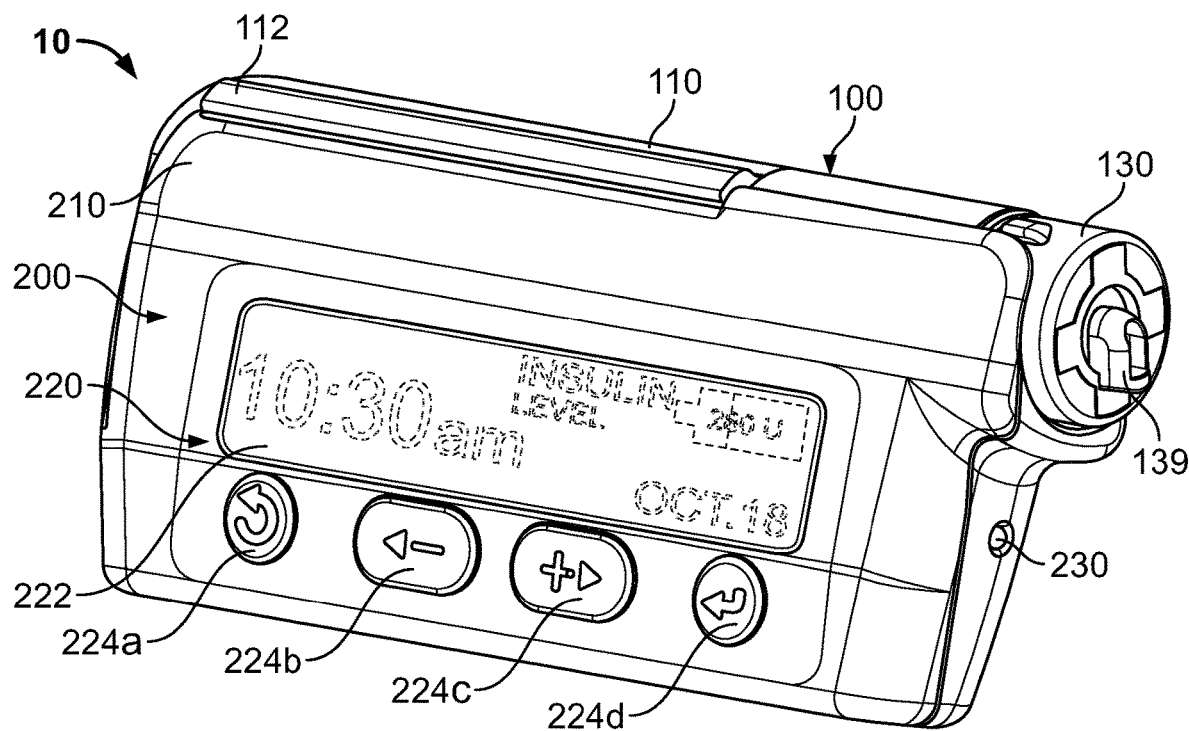
FIG. 2 is a perspective view of the infusion pump system of FIG. 1 in an assembled state.
Figure 3:
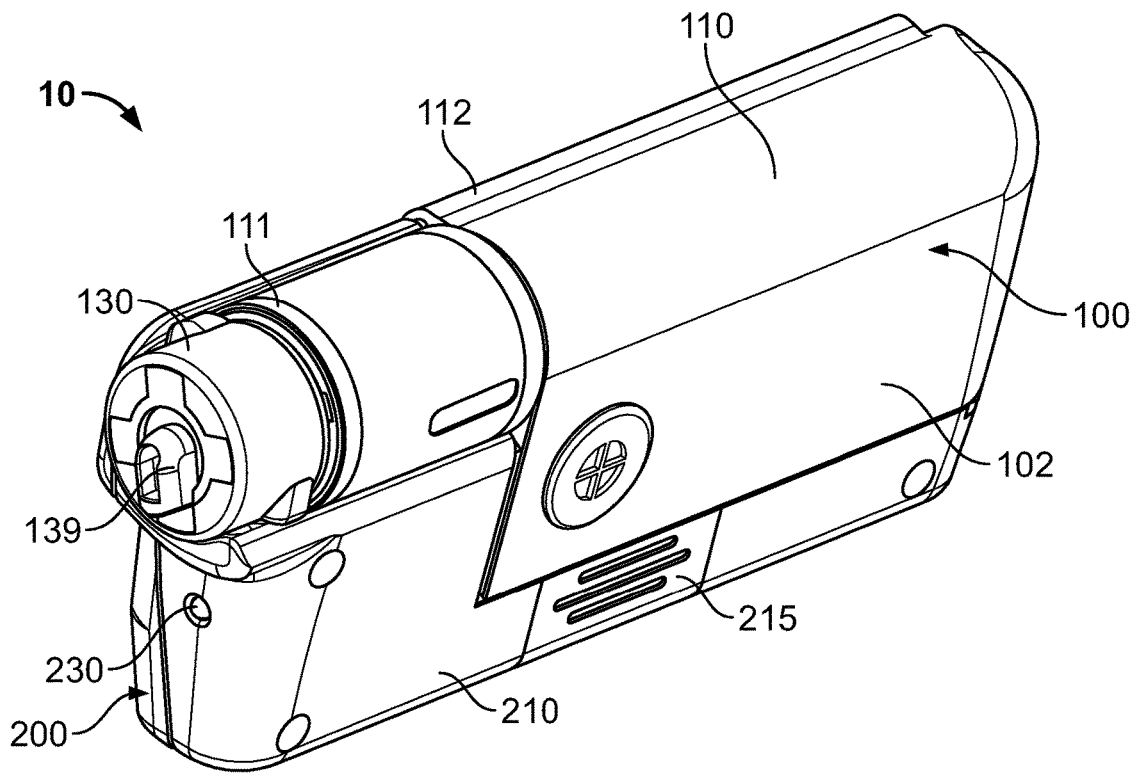
FIG. 3 is another perspective view of the infusion pump system of FIG. 2.

Referring to FIGS. 1-3, an infusion pump system 10 can include a pump device 100 and a controller device 200 that communicates with the pump device 100. The pump device 100 can include a housing structure 110 that defines a cavity 116 in which a fluid cartridge 120 can be received. The pump device 100 also can include a cap device 130 to retain the fluid cartridge 120 in the cavity 116 of the housing structure 110. The pump device 100 can include a drive system (described in more detail below) that advances a plunger 125 in the fluid cartridge 120 so as to dispense fluid therefrom. The controller device 200 communicates with the pump device 100 to control the operation of the drive system. When the controller device 200, the pump device 100 (including the cap device 130), and the fluid cartridge 120 are assembled together, the user can (in some embodiments) conveniently wear the infusion pump system 10 on the user's skin under clothing or in the user's pocket while receiving the fluid dispensed from the pump device 100.

The controller device 200 may be configured as a reusable component that provides electronics and a user interface to control the operation of the pump device 100. In such circumstances, the pump device 100 can be a disposable component that is disposed of after a single use. For example, as described in more detail below in connection with FIGS. 11-16, the pump device 100 can be a "one time use" component that is thrown away after the fluid cartridge 120 therein is exhausted. Thereafter, the user can removably attach a new pump device 100' (having a new medicine cartridge 120') to the reusable controller device 200 for the dispensation of fluid from a new fluid cartridge 120'. Accordingly, the user is permitted to reuse the controller device 200 (which may include complex or valuable electronics) while disposing of the relatively low-cost pump device 100 after each use. Such a pump system 10 can provide enhanced user safety as a new pump device 100 (and drive system therein) is employed with each new fluid cartridge 120.

The infusion pump system 10 may also include a rechargeable battery 245 (refer also to FIG. 17) in the controller device 200 and a charger battery 345 (refer also to FIGS. 17-19) in the pump device 100. The charger battery 345 can be disposable in that it can be discarded with the pump device 100 after exhaustion of the pump device 100. The rechargeable battery 245 can receive electrical energy from the charger battery 345 to maintain the rechargeable battery 245 at a charge greater than a threshold charge level. As described in more detail below, the rechargeable battery 245 can provide electrical energy to the drive system 300 (FIGS. 17-19) of the pump device 100 to dispense medicine to the patient. If the charger batter 345 in the pumps device becomes depleted, the controller device 200 can outputs an alert indicative of an estimated remaining power supply. This estimated remaining power can be based at least partially on the threshold charge level. Accordingly, infusion pump system 10 can incorporate two batteries 245 and 345 that can be used to accurately estimate the remaining power supply when one of the batteries (e.g., charger battery 345) becomes depleted. This features permits the estimation of the remaining power supply without necessarily detecting an actual charge level of the rechargeable battery 245, a function that can itself consume energy. In other embodiments, a monolithic infusion pump system can include a rechargeable energy source 245 and a replaceable battery 345, which can be individually removed from the infusion pump system.

As described in more detail below, the infusion pump system 10 may also conserve energy by using a pulse-width modulation (PWM) controller to output a pattern of pulses of voltage from the rechargeable battery 245 to the drive system. The use of PWM can reduce the total amount of power delivered to a drive system 300 (FIGS. 17-19) without losses normally incurred when a power source is limited by resistive means. This is because—in these embodiments that employ the PWM controller—the average power delivered is proportional to the modulation duty cycle. With a sufficiently high modulation rate, the drive system 300 (e.g., the rotational motor 320 in FIG. 17) may serve as a passive filter that smoothes the pulse train, thereby resulting in an average power waveform delivered to the drive system. Accordingly, the PWM controller can reduce the amount of energy drawn from the rechargeable battery 245 for a given drive cycle by delivering a pattern of voltage pulses to the drive system 300 such that the pulses average out to a delivered energy profile approximating an energy requirement profile for the drive system. Furthermore, in some embodiments, the controller device 200 can detect a voltage output level of the rechargeable battery 245 and select a voltage pulse duration (width) or frequency based on the voltage output level.

Briefly, in use, the pump device 100 is configured to removably attach to the controller device 200 in a manner that provides a secure fitting, an overall compact size, and a reliable electrical connection that is resistant to water migration. For example, as described in more detail below in connection with FIGS. 1-5, the controller device 200 can include a housing 210 having a number of features that mate with complementary features of the pump housing 110. In such circumstances, the controller device 200 can removably attach with the pump device 100 in a generally sideby-side configuration while not fully surrounding the pump housing 110. Accordingly, the pump device 100 and the controller device 200 can be separate components that fit together, but the overall size of the combined assembly is reduced because there is no requirement for one component (e.g., the controller device) to completely surround or envelop the second component (e.g., the pump device). The compact size permits the infusion pump system 10 to be discrete and portable (as described below in connection with FIGS. 6-8). Moreover, at least one of the pump device 100 or the controller device 200 can include a release member that facilitates an easy-to-use detachment and replacement process.

Referring again to FIGS. 1-3, the pump system 10 can be a medical infusion pump system that is configured to controllably dispense a medicine from the cartridge 120. As such, the fluid cartridge 120 can contain a medicine 126 (FIG. 1) to be infused into the tissue or vasculature of a targeted individual, such as a human or animal patient. For example, the pump device 100 can be adapted to receive a medicine cartridge 120 in the form of a carpule that is preloaded with insulin or another medicine for use in the treatment of Diabetes (e.g., Byetta®, Symlin®, or others). Such a cartridge 120 may be supplied, for example, by Eli Lilly and Co. of Indianapolis, Ind. Other examples of medicines contained in the fluid cartridge 120 include: pain relief drugs, hormone therapy, blood pressure treatments, anti-emetics, osteoporosis treatments, or other injectable medicines. The fluid cartridge 120 may have other configurations. For example, the fluid cartridge 120 may comprise a reservoir that is integral with the pump housing structure 110 (e.g., the fluid cartridge 120 can be defined by one or more walls of the pump housing structure 110 that surround a plunger to define a reservoir in which the medicine is injected or otherwise received).

In some embodiments, the pump device 100 can include one or more structures that interfere with the removal of the medicine cartridge 120 after the medicine cartridge 120 is inserted into the cavity 116. For example, as shown in FIG. 1, the pump housing structure 110 can include one or more retainer wings 119 that at least partially extend into the cavity 116 to engage a portion of the medicine cartridge 120 when the medicine cartridge 120 is installed therein. Such a configuration may facilitate the "one-time-use" feature of the pump device 100. In some embodiments, the retainer wings 119 can interfere with attempts to remove the medicine cartridge 120 from the pump device 100, thus ensuring that the pump device 100 will be discarded along with the medicine cartridge 120 after the medicine cartridge 120 is emptied, expired, or otherwise exhausted. Accordingly, the pump device 100 can operate in a tamper-resistant and safe manner because the pump device 100 can be designed with predetermined life expectancy (e.g., the "one-time-use" feature in which the pump device is discarded after the medicine cartridge 120 is emptied, expired, or otherwise exhausted).

Still referring to FIGS. 1-3, the controller device 200 can be removably attached to the pump device 100 so that the two components are mechanically mounted to one another in a fixed relationship. Such a mechanical mounting can form an electrical connection between the removable controller device 200 and the pump device 100. For example, the controller device 200 can be in electrical communication with a portion of a drive system (not shown in FIGS. 1-3) of the pump device 100. As described in more detail below, the pump device 100 can include a drive system that causes controlled dispensation of the medicine or other fluid from the cartridge 120. In some embodiments, the drive system incrementally advances a piston rod (not shown in FIGS. 1-3) longitudinally into the cartridge 120 so that the fluid is forced out of an output end 122. A septum 121 (FIG. 1) at the output end 122 of the fluid cartridge 120 can be pierced to permit fluid outflow when the cap device 130 is connected to the pump housing structure 110 (described in more detail below). Thus, when the pump device 100 and the controller device 200 are attached and thereby electrically connected, the controller device 200 communicates electronic control signals via a hardwire-connection (e.g., electrical contacts or the like) to the drive system or other components of the pump device 100. In response to the electrical control signals from the controller device 200, the drive system of the pump device 100 causes medicine to incrementally dispense from the medicine cartridge 120.

As shown in FIG. 1, the pump device 100 can include an electrical connector 118 (e.g., having conductive pads, pins, and the like) that are exposed to the controller device 200 and that mate with a complementary electrical connector (refer to connector 218 in FIG. 4) on the adjacent face of the controller device 200. The electrical connectors 118 and 218 provide the electrical communication between the control circuitry (refer, for example, to FIG. 15) housed in the controller device 200 and at least a portion of the drive system or other components of the pump device 100. For example, in some embodiments, the electrical connectors 118 and 218 can permit the transmission of electrical control signals to the pump device 100 and the reception of feedback signals (e.g., sensor signals) from particular components within the pump device 100. Furthermore, as described in more detail below, the infusion pump system 10 can include a gasket 140 that provides a seal that is resistant to migration of external contaminants when the pump device 100 is attached to the controller device 200. Thus, in some embodiments, the infusion pump system 10 can be assembled into a water resistant configuration that protects the electrical interconnection from water migration (e.g., if the user encounters water while carrying the pump system 10).

Still referring to FIGS. 1-3, the controller device 200 can include a user interface 220 that permits a user to monitor the operation of the pump device 100. In some embodiments, the user interface 220 can include a display device 222 and one or more user-selectable buttons (e.g., four buttons 224a, 224b, 224c, and 224d in this embodiment). The display device 222 can include an active area in which numerals, text, symbols, images, or a combination thereof can be displayed (refer, for example, to FIG. 2). For example, the display device 222 can be used to communicate a number of settings or menu options for the infusion pump system 10. In this embodiment, the user may press one or more of the buttons 224a, 224b, 224c, and 224d to shuffle through a number of menus or program screens that show particular settings and data (e.g., review data that shows the medicine dispensing rate, the total amount of medicine dispensed in a given time period, the amount of medicine scheduled to be dispensed at a particular time or date, the approximate amount of medicine remaining in the cartridge 120, or the like). In some embodiments, the user can adjust the settings or otherwise program the controller device 200 by pressing one or more buttons 224a, 224b, 224c, and 224d of the user interface 220. For example, in embodiments of the infusion pump system 10 configured to dispense insulin, the user may press one or more of the buttons 224a, 224b, 224c, and 224d to change the dispensation rate of insulin or to request that a bolus of insulin be dispensed immediately or at a scheduled, later time.

Accordingly, when the controller device 200 is connected to the pump device 100, the user can be provided with the opportunity to readily monitor the infusion pump operation by simply viewing the user interface 220 of the controller device 200 connected to the pump device 100. Such monitoring capabilities may provide comfort to a user who may have urgent questions about the current operation of the pump device 100. Also, in these embodiments, there may be no need for the user to carry and operate a separate module to monitor the operation of the infusion pump device 100, thereby simplifying the monitoring process and reducing the number of devices that must be carried by the user. If a need arises in which the user desires to monitor the operation of the pump device 100 or to adjust the settings of the pump system 10 (e.g., to request a bolus amount of medicine), the user can readily operate the user interface 220 of the controller device 200, which is removably attached to the pump device 100, without the requirement of locating and operating a separate monitoring module.

Figure 4:
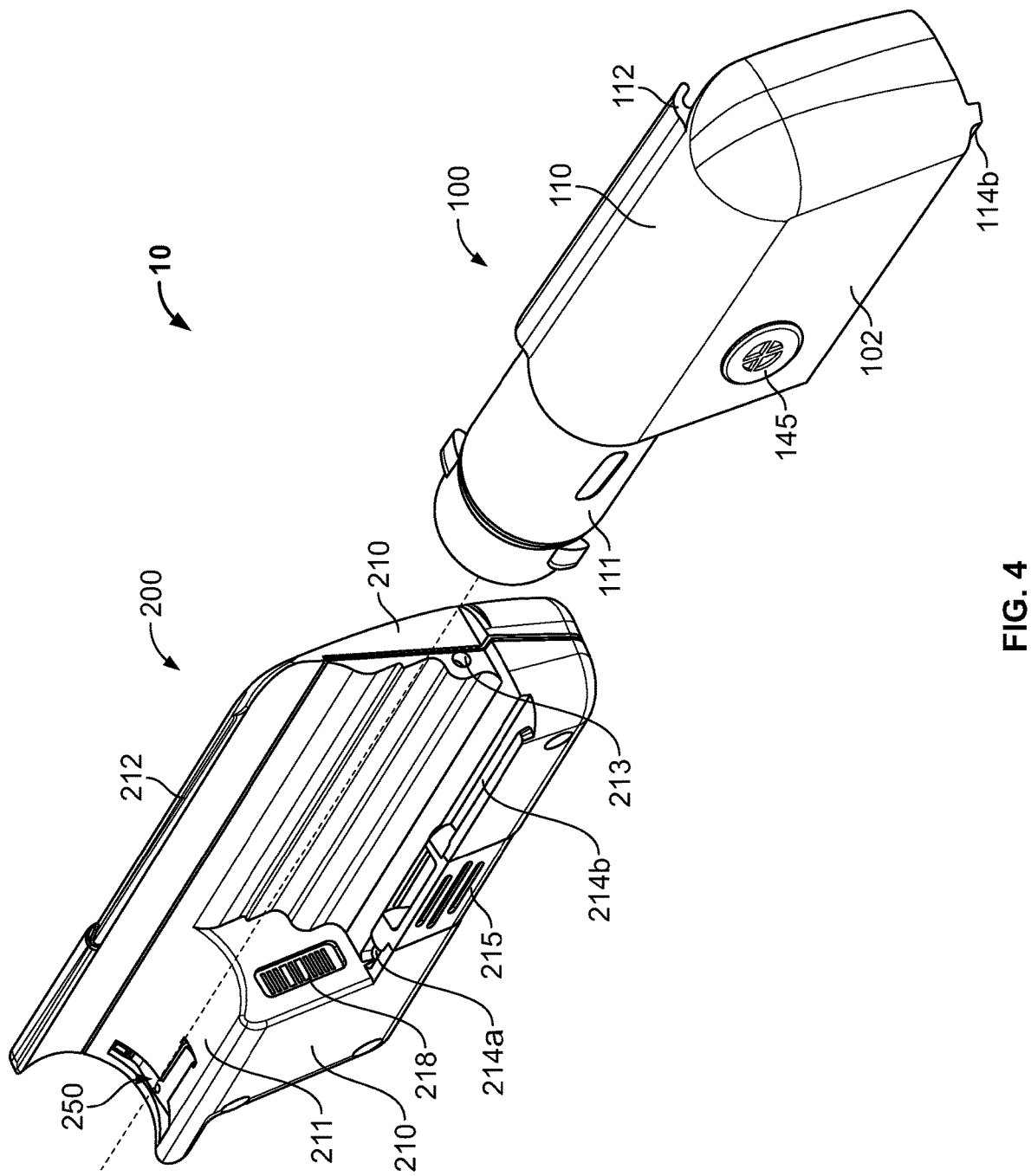
FIG. 4 is a perspective view of the infusion pump system of FIG. 1 in a detached state.
Figure 5:
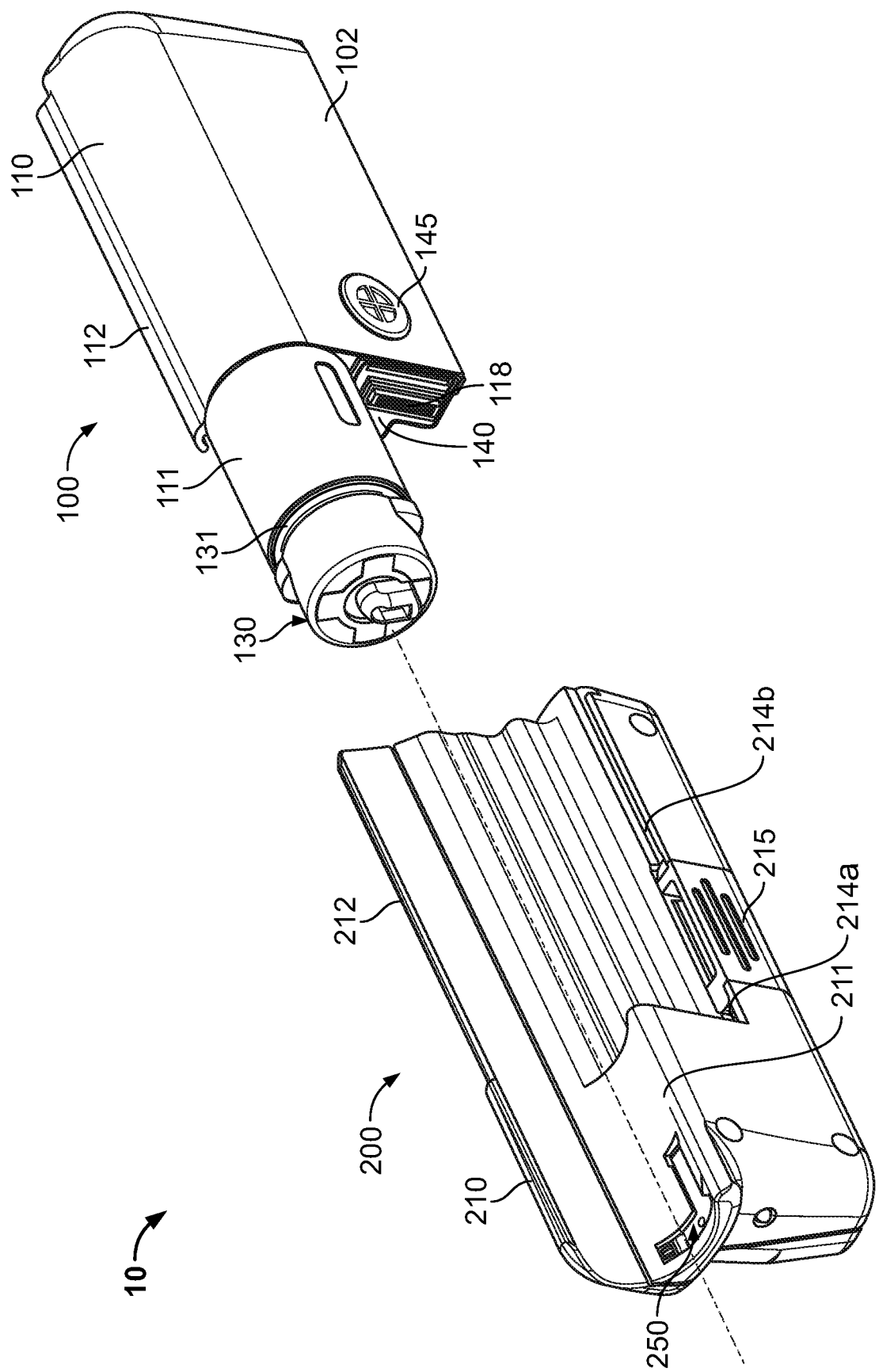
FIG. 5 is another perspective view of the infusion pump system on FIG. 4.

Referring now to FIGS. 4-5, when the infusion pump system 10 operates, the controller device 200 can be removably attached to the pump device 100 in a side-by-side arrangement. For example, the pump device 100 may be moved in a longitudinal direction (e.g., refer to direction 219 in FIG. 13) toward the controller device 200 until the complementary features connect and secure the separate components in the side-by-side arrangement. In these circumstances, the pump device 100 and the controller device 200 can be separate components that fit together, but the overall size of the combined assembly can be reduced because there is no requirement for one component (e.g., the controller device or pump device) to surround or envelop the second component (e.g., the pump device or controller device). Moreover, in some embodiments, the pump device 100 and controller device 200 can be readily attached together with a "one-movement" process that is convenient to the user.

The controller device 200 can include a controller housing structure 210 having a number of features that are configured to mate with complementary features of the pump housing structure 110 so as to form a releasable mechanical connection. For example, the pump housing structure 110 can include a barrel 111 that mates with a complementary barrel channel 211 of the controller housing 210. Also, the pump housing 110 can include slider channel 112 that slidably engages a complementary rail 212 defined by the controller housing 210. The slider channel 112 can guide the relative motion between the pump device 100 and the controller device 200 in the longitudinal direction during the attachment process. Similarly, the pump housing 110 can include a segmented rail 114*a-b* (FIG. 1) that mates with a guide channel 214*a-b* to direct the relative longitudinal motion between the pump device 100 and the controller device 200. As described in more detail below, the segmented rails 114*a-b* can interact with the release member 215 so as to releasably secure the pump device 100 into assembly with the controller device 200. In addition, the pump housing 110 can include an extension 113 (FIG. 1) that mates with a depression 213 (FIG. 4) in the controller housing 210 when the pump device 100 is fully attached to the controller device 200. It should be understood that, in other embodiments, other features or connector devices can be used to facilitate the side-by-side mounting arrangement. These other features or connector devices can include, for example, magnetic attachment device, mating tongues and grooves, mounting protrusions that friction fit into mating cavities, or the like.

Still referring to FIGS. 4-5, the pump device 100 and the controller device 200 can be attached in a manner that is resistant to migration of external contaminants (e.g., water, dirt, and the like) both into the pump housing structure 110 and the controller housing structure 210. For example, when the pump device 100 is advanced in the longitudinal direction toward the controller device 200 (as guided by the slider channel 112 and the segmented rails 114*a-b*), the electrical connector 118 (FIG. 5) of the pump device 100 is directed toward engagement with the mating connector 218 (FIG. 4) of the controller device 200. When the connectors 118 and 218 join together to form the electrical connection, the gasket 140 is compressed between the adjacent surfaces of the pump housing 110 and the controller housing 210. The gasket 140 thereby forms a water-resistant seal between the ambient environment and the mated connectors 118 and 218. Accordingly, in particular circumstances, the infusion pump system 10 can be assembled into a "water tight" configuration that protects sensitive internal components from water migration in the event that the user encounters water while wearing the pump system 10. In one example, the gasket 140 can resist migration of water to the electrical connectors 118 and 218 even when the system 10 is submerged underwater (e.g., in a pool, in a bath, or the like) for an extended period of time, such as at least 10 minutes, at least 30 minutes, at least one hour, at least two hours, and preferably at least four hours.

In addition, other paths for migration of external contaminants into the assembled pump system 10 can be sealed. For example, the infusion pump system 10 can include one or more seals that are arranged to hinder migration of external contaminants between the cap device 130 and the pump housing 110 into the cavity 116 of the pump device 100. In some embodiments, the seal 131 arranged between the cap device 130 and the barrel 111 can provide an effective water-resistant seal against water migration into the cavity. As such, the medicine cartridge 120 and pump drive system (not shown in FIGS. 4-5) can be protected during operation.

Still referring to FIGS. 4-5, some embodiments of the infusion pump system 10 may employ a power source arranged in pump device 100 or the controller device 200 that draws upon surrounding air for optimum operation. Because the controller device 200 and the pump device 100 may be sealed to resist water migration during normal usage, a water-resistant vent instrument 145 can be used to provide the air to the power source without permitting migration of water therethrough. For example, the pump device 100 can contain a first power source 345 in the form of a zinc-air cell battery (refer to FIG. 17), which draws upon the surrounding air during operation. When the pump device 100 is in use, the pump housing 110 can be sealed to protect the internal drive system and medicine cartridge from water migration. As such, the pump housing 110 can include a water-resistant vent instrument 145 disposed proximate to the first power source 345 (e.g., a zinc air cell battery) so that some air may pass through the vent 145 and toward the first power source 345. The water-resistant vent instrument 145 can include one or more layers of a material that is permeable to air and resistant to passage of liquids such as water. For example, the water-resistant vent instrument 145 can include one or more layers of a GORE-TEX material to resist the migration of water into the pump device while permitting the passage of air toward the battery.

Accordingly, the pump device 100 and the controller device 200 can be mounted to one another so that the assembled system 10 is resistant to water migration both into the pump housing structure 110 and the controller housing structure 210. Such a configuration can also provide water-resistant protection for the electrical connection between the pump device 100 and the controller device 200. Thus, the sensitive internal components in the controller device 200 and the pump device 100 can be reliably protected from water migration if the user encounters water (e.g., rain, incidental splashing, and the like) while using the pump system 10.

Figure 6:
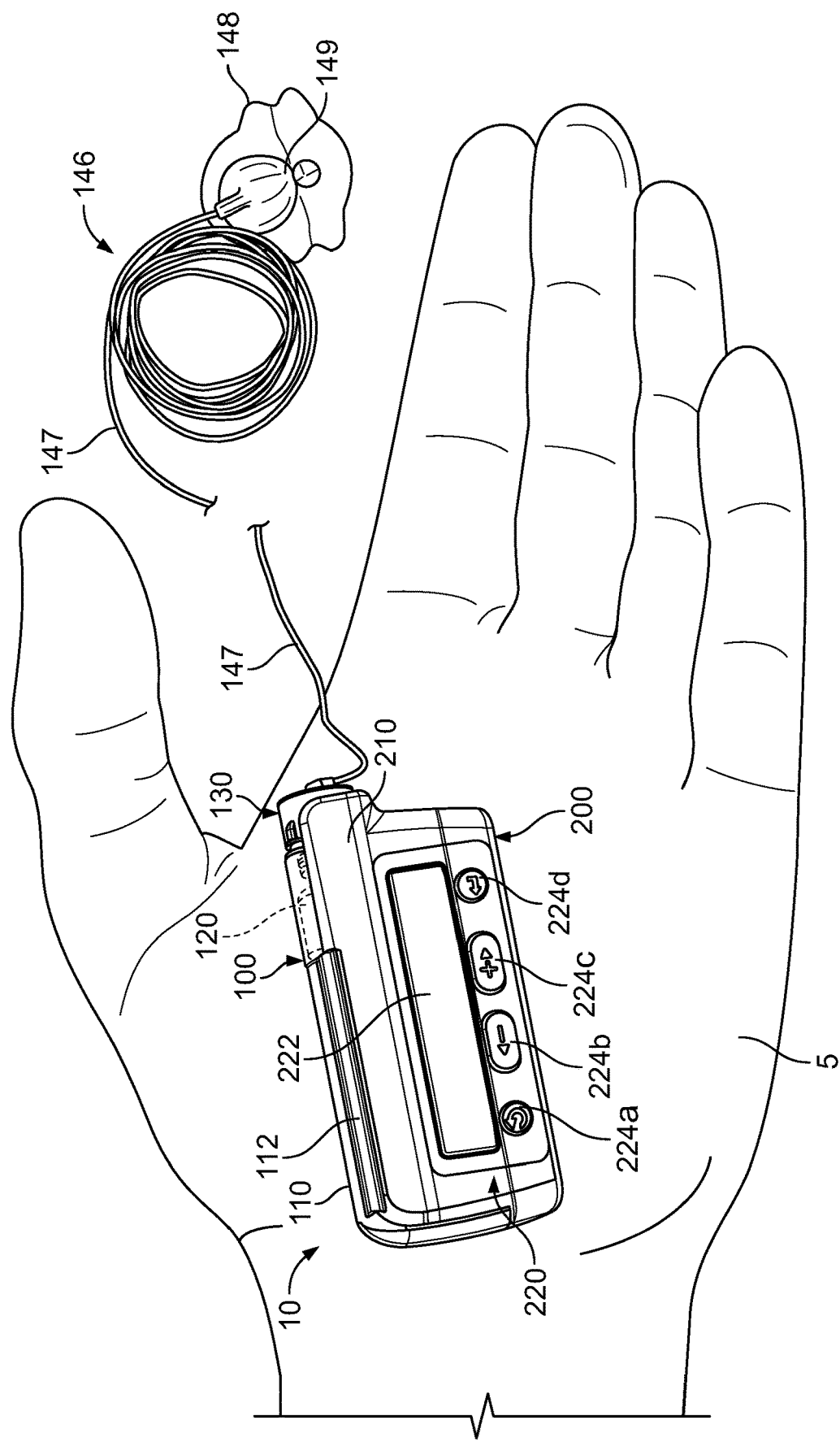
FIG. 6 is a perspective view of an infusion pump system, in accordance with some embodiments.
Figure 7:
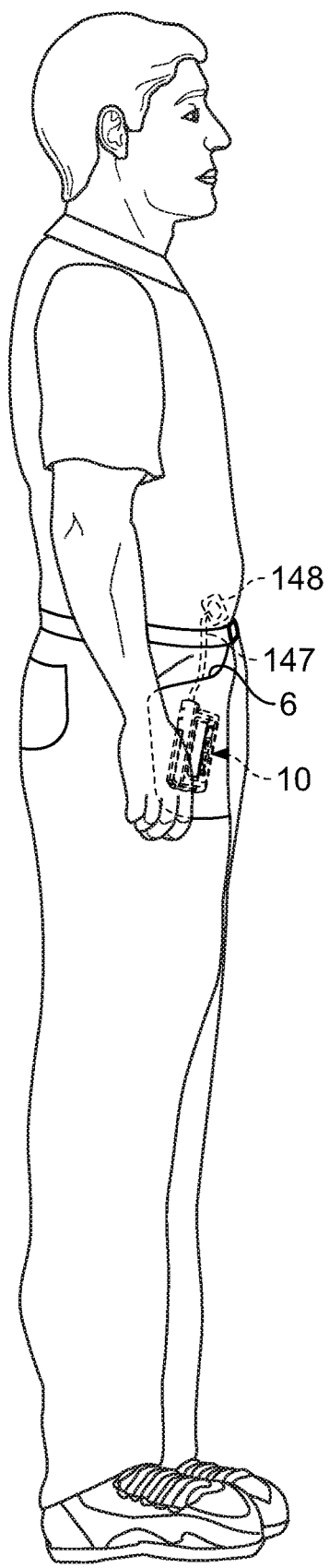
FIG. 7 is a perspective view of the infusion pump system of FIG. 6 worn on the clothing of a user.
Figure 8:
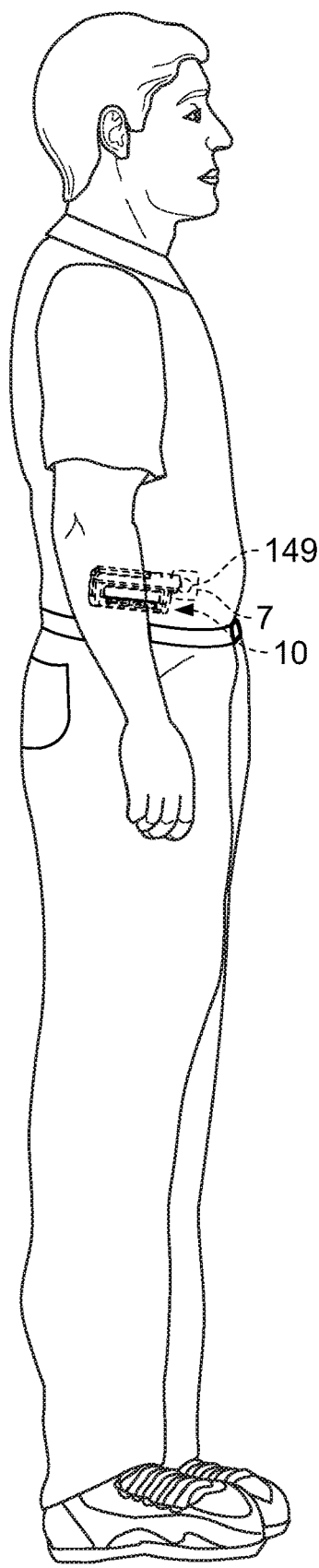
FIG. 8 is a perspective view of an infusion pump system worn on skin of a user, in accordance with particular embodiments.
Figure 9:
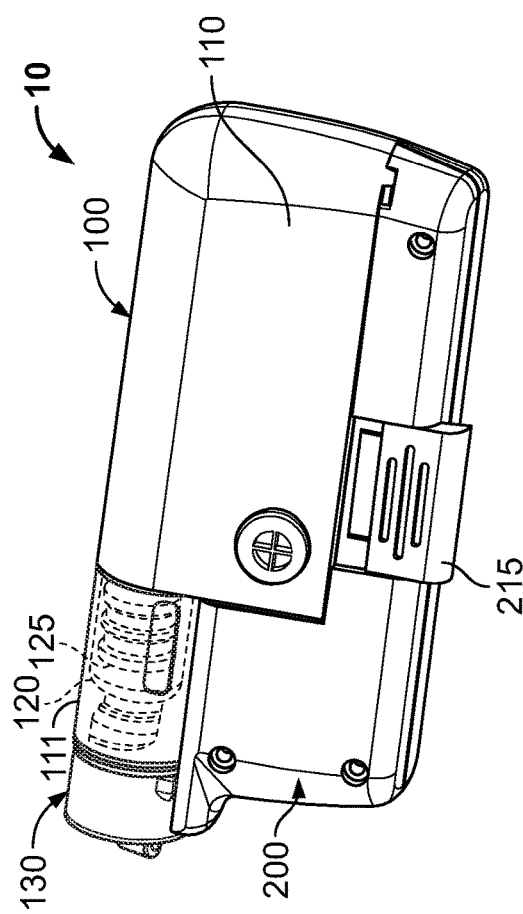
FIGS. 9-10 are perspective views of a pump device being detached from a controller device, in accordance with some embodiments.
Figure 10:
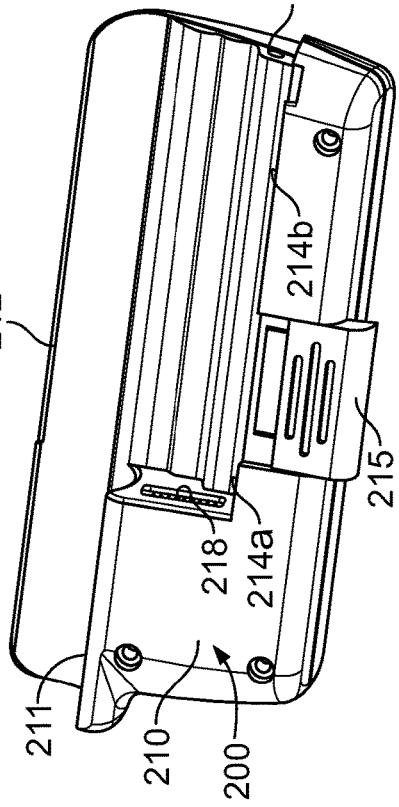
Figure 10:
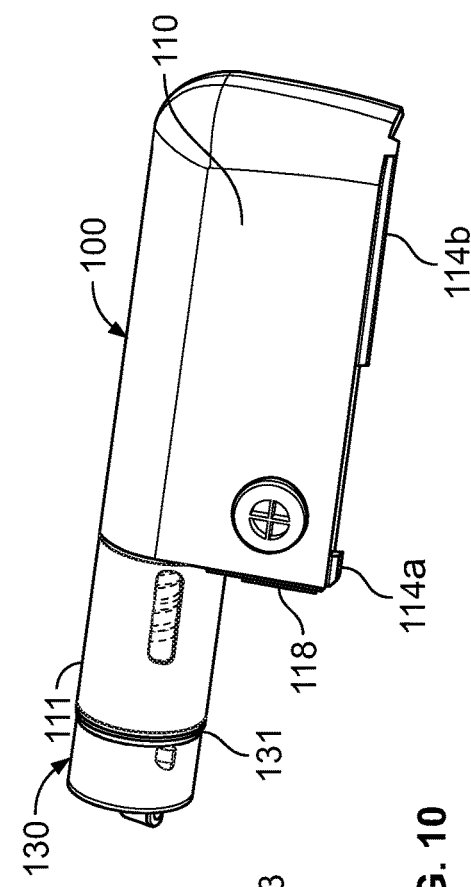

Referring to FIGS. 6-8, the infusion pump system 10 can be configured to be portable and can be wearable and concealable. For example, a user can conveniently wear the infusion pump system 10 on the user's skin (e.g., skin adhesive) underneath the user's clothing or carry the pump device 100 in the user's pocket (or other portable location) while receiving the medicine dispensed from the pump device 100. As described below in connection with FIGS. 20-26, the drive system of the pump device 100 can be arranged in a compact manner so that the pump device 100 has a reduced length. For example, in the circumstances in which the medicine cartridge 120 has a length of about 6 cm to about 7 cm (about 6.4 cm in one embodiment), the overall length of the pump housing structure 110 (which contains medicine cartridge and the drive system) can be about 7 cm to about 10 cm and about 7 cm to about 9 cm (about 8.3 cm or less in some embodiments). In addition, the pump housing structure 110 can have an overall height of about 2 cm to about 4 cm (about 3.1 cm or less in some embodiments) and an overall thickness of about 8 mm to about 20 mm (about 17.5 mm or less in one embodiment).

The pump system 10 is shown in FIG. 6 as being held in a user's hand 5 so as to illustrate an exemplary size of the system 10 in accordance with some embodiments. This embodiment of the infusion pump system 10 is compact so that the user can wear the portable infusion pump system 10 (e.g., in the user's pocket, connected to a belt clip, adhered to the user's skin, or the like) without the need for carrying and operating a separate module. In such embodiments, the cap device 130 of the pump device 100 can be configured to mate with an infusion set 146. In general, the infusion set 146 can be a tubing system that connects the infusion pump system 10 to the tissue or vasculature of the user (e.g., to deliver medicine into the tissue or vasculature under the user's skin). The infusion set 146 can include a flexible tube 147 that extends from the pump device 100 to a subcutaneous cannula 149 retained by a skin adhesive patch 148 that secures the subcutaneous cannula 149 to the infusion site. The skin adhesive patch 148 can retain the infusion cannula 149 in fluid communication with the tissue or vasculature of the patient so that the medicine dispensed through the tube 147 passes through the cannula 149 and into the user's body. The cap device 130 can provide fluid communication between the output end 122 (FIG. 1) of the medicine cartridge 120 and the tube 147 of the infusion set 146.

Referring to FIG. 7, in some embodiments, the infusion pump system 10 can be pocket-sized so that the pump device 100 and controller device 200 can be worn in the user's pocket 6 or in another portion of the user's clothing. In some circumstances, the user may desire to wear the pump system 10 in a more discrete manner. Accordingly, the user can pass the tube 147 from the pocket 6, under the user's clothing, and to the infusion site where the adhesive patch 148 can be positioned. As such, the pump system 10 can be used to delivery medicine to the tissues or vasculature of the user in a portable, concealable, and discrete manner.

Referring to FIG. 8, in some embodiments, the infusion pump system 10 can be configured to adhere to the user's skin 7 directly at the location in which the skin is penetrated for medicine infusion. For example, a rear surface 102 (FIG. 3) of the pump device 100 can include a skin adhesive patch so that the pump device 100 can be physically adhered to the skin of the user at a particular location. In these embodiments, the cap device 130 can have a configuration in which medicine passes directly from the cap device 130 into an infusion cannula 149 that is penetrated into the user's skin. In some examples, the user can temporarily detach the controller device 200 (while the pump device 100 remains adhered to the skin 7) so as to view and interact with the user interface 220.

Referring now to FIGS. 11-16, the infusion pump system 10 can be operated such that the pump device 100 is a disposable, non-reusable component while the controller device 200 is a reusable component. In these circumstances, the pump device 100 may be configured as a "one-time-use" device that is discarded after the medicine cartridge is emptied, expired, or otherwise exhausted. Thus, in some embodiments, the pump device 100 can be designed to have an expected operational life of about 1 day to about 30 days, about 1 day to about 20 days, about 1 to about 14 days, or about 1 day to about 7 days—depending on the volume of medicine in the cartridge 120, the dispensation patterns that are selected for the individual user, and other factors. For example, a medicine cartridge 120 containing insulin can have an expected usage life about 7 days after the cartridge is removed from a refrigerated state and the septum 121 is punctured. In some circumstances, the dispensation pattern selected by the user can cause the insulin to be emptied from the medicine cartridge 120 before the 7-day period. If the insulin is not emptied from the medicine cartridge 120 after the 7-day period, the remaining insulin can become expired sometime thereafter. In either case, the pump device 100 and the medicine cartridge 120 therein can be discarded after exhaustion of the medicine cartridge 120 (e.g., after being emptied, expired, or otherwise not available for use).

The controller device 200, however, may be reused with subsequent new pump devices 100' and new medicine cartridges 120'. As such, the control circuitry, the user interface components, and other components that may have relatively higher manufacturing costs can be reused over a longer period of time. For example, in some embodiments, the controller device 200 can be designed to have an expected operational life of about 1 year to about 7 years, about 2 years to about 6 years, or about 3 years to about 5 years—depending on a number of factors including the usage conditions for the individual user. Accordingly, the user can be permitted to reuse the controller device 200 (which can include complex or valuable electronics) while disposing of the relatively low-cost pump device 100 after each use. Such a pump system 10 can provide enhanced user safety as a new pump device 100' (and drive system therein) is employed with each new fluid cartridge 120.

Figure 11:
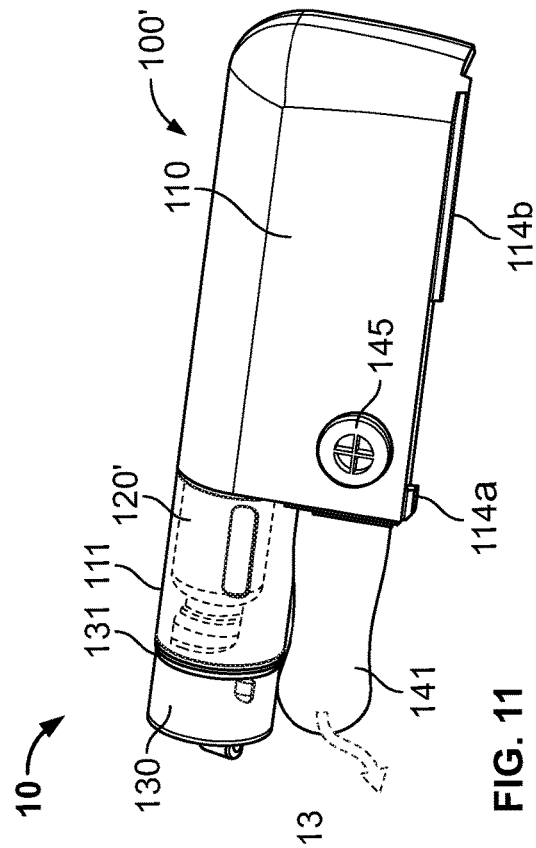
FIGS. 11-12 are perspective views of the pump device of FIGS. 9-10 being discarded and the controller device of FIGS. 9-10 being reused with a new pump device.
Figure 12:
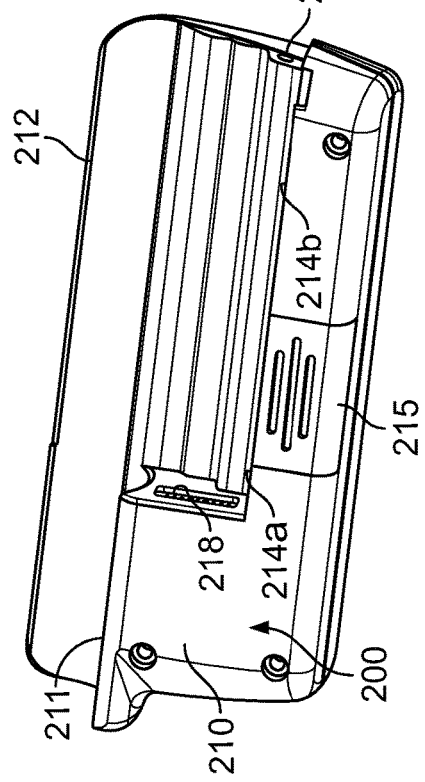
Figure 12:
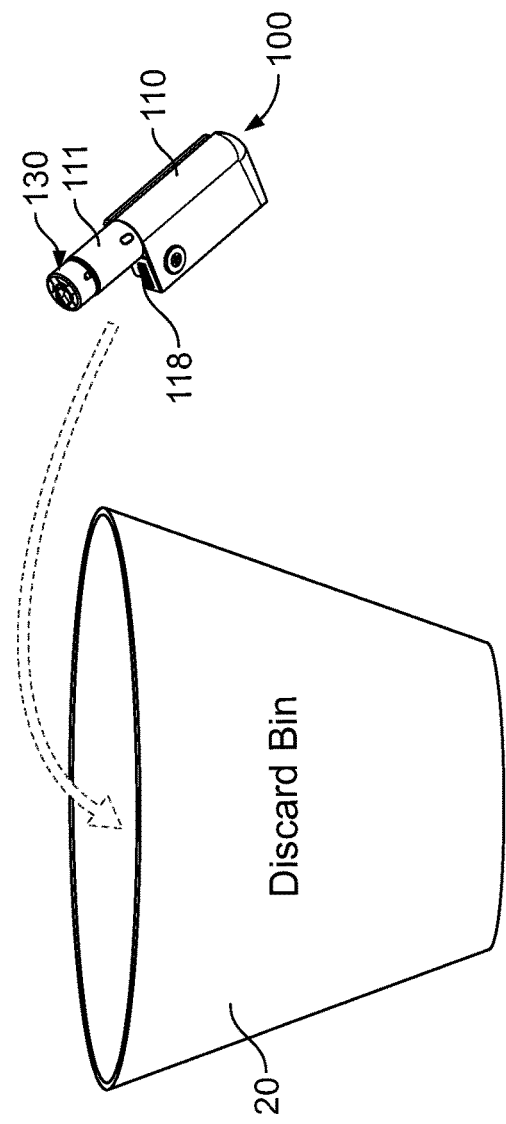

Referring to FIGS. 11-12, the same controller device 200 can be reused with a new pump device 100' having a new medicine cartridge 120' retained therein, and the previously used pump device 100 can be discarded with the exhausted medicine cartridge 120. The new pump device 100' (FIG. 11) can have a similar appearance, form factor, and operation as the previously used pump device 100, and thus the new pump device 100' can be readily attached to the controller device 200 for controlled dispensation of medicine from the new medicine cartridge 120'. In some embodiments, the user can prepare the new pump device 100 for use with the controller device 200. For example, the user may insert the new medicine cartridge 120' in the cavity 116 of the new pump device 100' and then join the cap device 130 to the pump housing to retain the new medicine cartridge 120' therein (refer, for example, to FIG. 1). Although the tubing 147 of the infusion set 146 is not shown in FIG. 11, it should be understood that the tubing 147 can be attached to the cap device 130 prior to the cap device 130 being joined with the housing 110. For example, a new infusion set 146 can be connected to the cap device 130 so that the tubing 147 can be primed (e.g., a selected function of the pump device 100 controlled by the controller device 200) before attaching the infusion set patch to the user's skin. As shown in FIG. 11, the new medicine cartridge 120' may be filled with medicine such that the plunger 125 is not viewable through the barrel 111.

Figure 13:
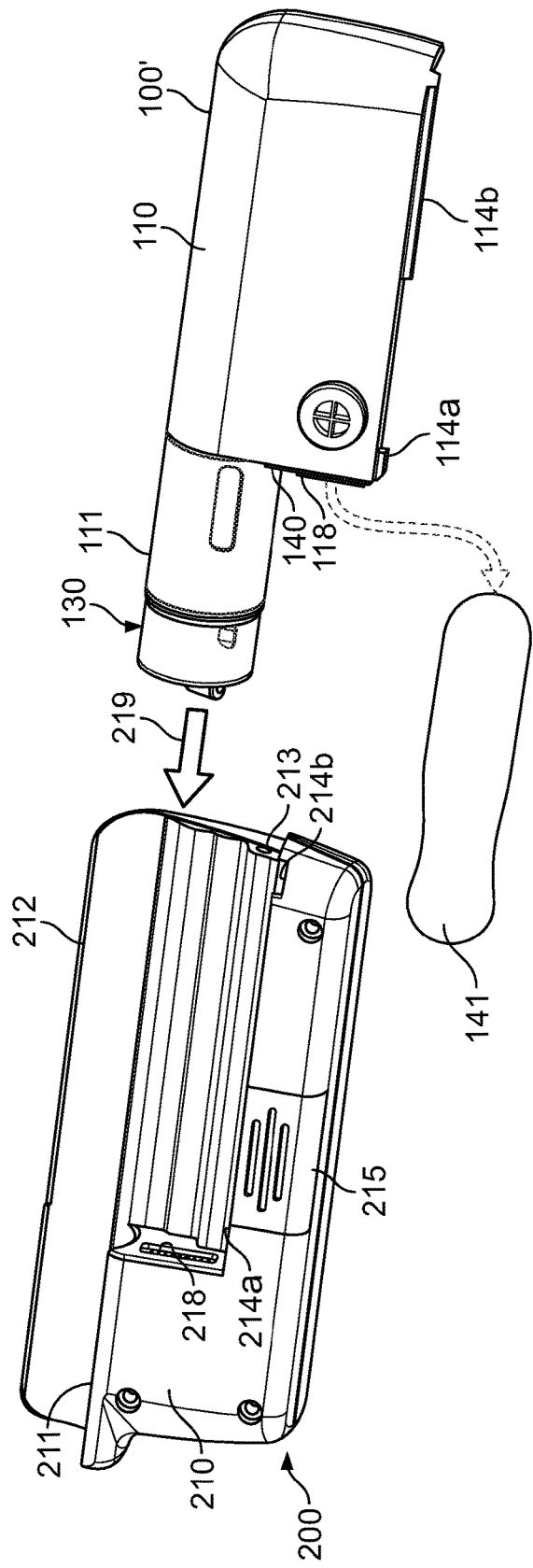
FIGS. 13-14 are perspective views of the new pump device of FIG. 11 being attached to the controller device of FIG. 11.
Figure 14:
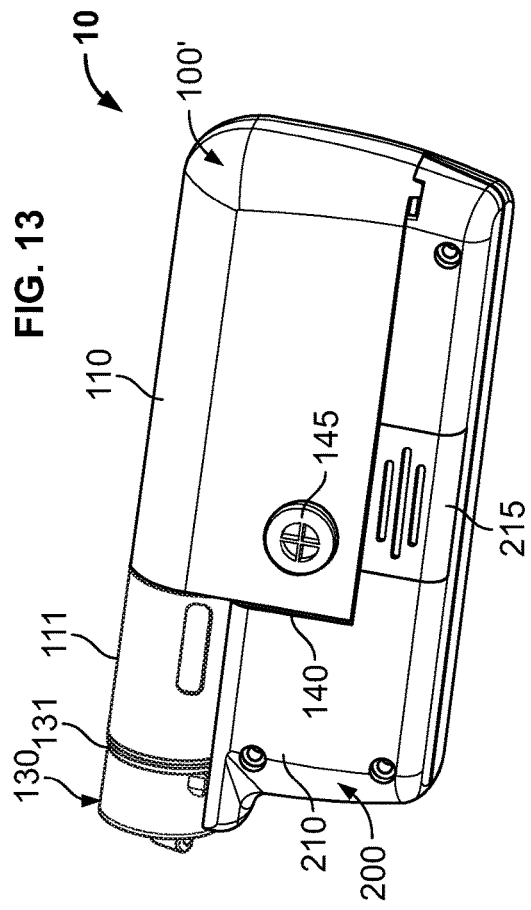

Referring to FIGS. 13-14, the new pump device 100' can be removably attached to the controller device 200 to assemble into the infusion pump system 10 for delivery of medicine to the user. Before the pump device 100 is electrically connected with the controller device 200, the user may prepare the new pump device 100' for use by pulling the removable tab 141 away from the pump housing 110. The new pump device 100' can include the removable tab 141 to seal the battery in the unused pump device 100' and thereby maintain the battery in a storage mode (refer, for example, to FIG. 11 in which the removable tab 141 is arranged to cover an internal face of the vent 115). As described in more detail below, when the new pump device 100' is prepared for usage, the removable tab 141 can be pulled away from the pump housing 110 (and away from the battery therein), which switches the battery into an activation mode. Thus, the shelf-life of the pump device 100' (prior to usage with the controller device 200) may be extended by sealing the battery in a storage mode because little, if any, energy is dissipated from the battery when in the storage mode.

As previously described, the guided motion in the longitudinal direction 219 provides the user with a convenient "one-movement" process to attach the pump device 100' and the controller device 200. For example, the user can readily slide the pump device 100' and the controller device 200 toward one another in a single movement (e.g., in the longitudinal direction) that causes both a physical connection and an electrical connection. Thus, the infusion pump system 10 can permit users to readily join the pump device 100' and the controller device 200 without compound or otherwise difficult hand movements—a feature that can be beneficial to child users or to elderly users.

Figure 15:
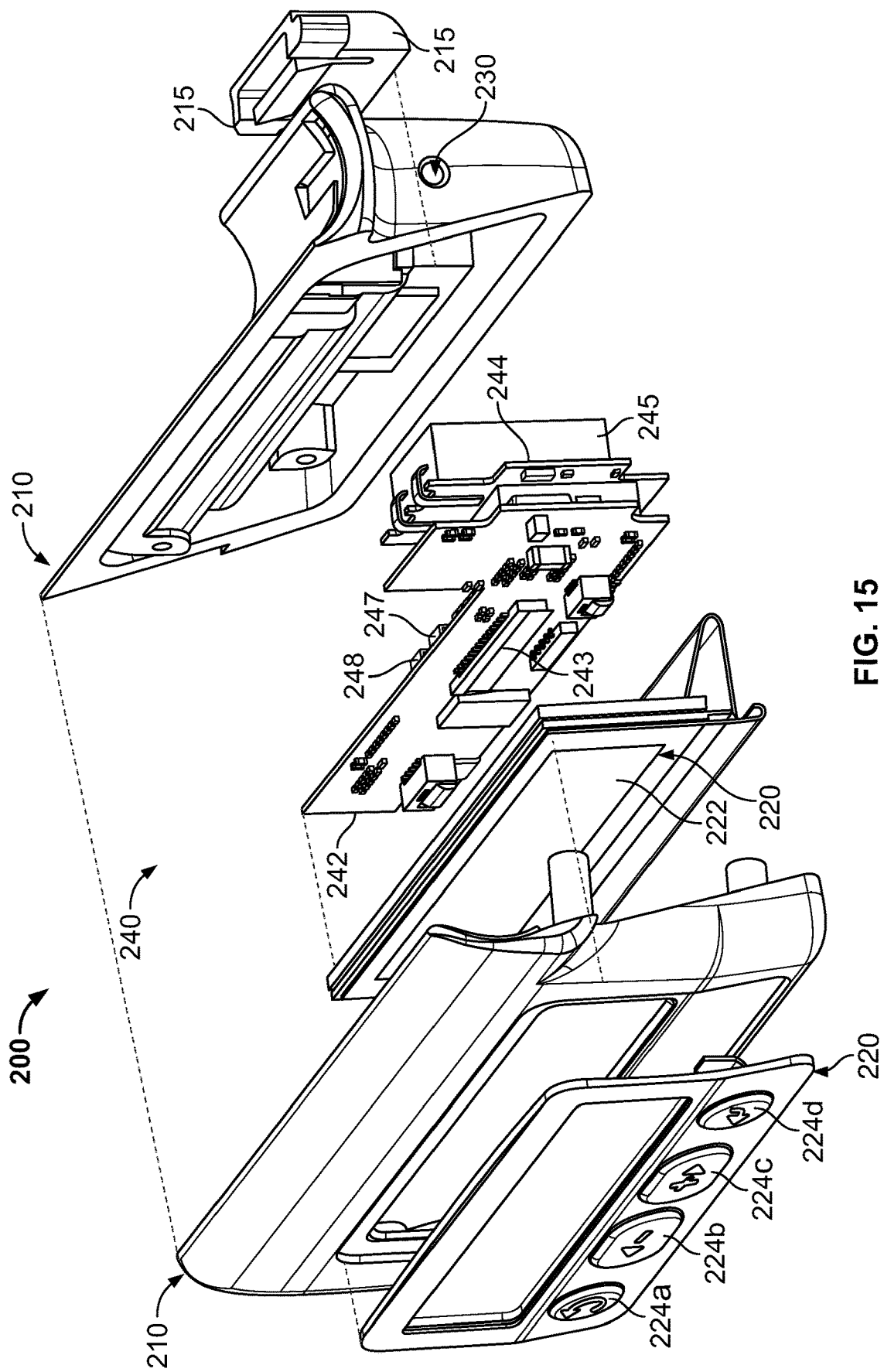
FIG. 15 is an exploded perspective view of a controller device for an infusion pump system, in accordance with some embodiments.

Referring now to FIG. 15, the controller device 200 (shown in an exploded view) houses a number of components that can be reused with a series of successive pump devices 100. In particular, the controller device 200 can include control circuitry 240 arranged in the controller housing 210 configured to communicate control signals to the drive system of the pump device 100. In some embodiments, the control circuitry 240 can include a main processor board 242 in communication with a power supply board 244. The control circuitry 240 can include at least one processor 243 that coordinates the electrical communication to and/or from the controller device 200 (e.g., communication between the controller device 200 and the pump device 100). The processor 243 can be arranged on the main processor board 242 along with a number of other electrical components, such as memory devices. It should be understood that, although the main processor board 242 is depicted as a printed circuit board, the main processor board can have other forms, including multiple boards, a flexible circuit substrate, and other configurations that permit the processor 243 to operate. The control circuitry 240 can be programmable, i.e., the user may provide one or more instructions to adjust a number of settings for the operation of the infusion pump system 10. Such settings may be stored in the memory devices arranged in the control circuitry 240. Furthermore, the control circuitry 240 can include one or more dedicated memory devices storing executable software instructions for the processor 243. The control circuitry 240 can include other components, such as sensors, that are electrically connected to the main processor board 242. For example, at least a portion of the occlusion sensor 250 (not shown in FIG. 15) can be electrically connected to the main processor board 242 via a flexible circuit substrate and/or one or more wires.

Still referring to FIG. 15, the user interface 220 of the controller device 200 can include input components and/or output components, that are electrically connected to the control circuitry 240. For example, the user interface 220 can include a display device 222 having an active area that outputs information to a user and four buttons 224a-d that receive input from the user. Here, the display device 222 can be used to communicate a number of settings or menu options for the infusion pump system 10. In some embodiments, the control circuitry 240 can receive input commands from a user's button selections and thereby cause the display device 222 to output a number of menus or program screens that show particular settings and data (e.g., review data that shows the medicine dispensing rate, the total amount of medicine dispensed in a given time period, the amount of medicine scheduled to be dispensed at a particular time or date, the approximate amount of medicine remaining the cartridge 120, the amount of battery life remaining, or the like). As previously described, the controller circuit 240 can be programmable to cause the controller circuit 240 to change any one of a number of settings for the infusion pump system 100.

Some embodiments of the control circuitry 240 can include a cable connector (e.g., a USB connection port or another data cable port) that is accessible on an external portion of the controller housing 210. As such, a cable can be connected to the control circuitry 240 to upload data or program settings to the controller circuit or to download data from the control circuitry 240. For example, historical data of medicine delivery can be downloaded from the control circuitry 240 (via the cable connector) to a computer system of a physician or a user for purposes of analysis and program adjustments. Optionally, the data cable can also provide recharging power.

In some embodiments, the pump device 100 can include a first power source 345 (refer to FIG. 17) capable of transmitting electrical energy to the controller device 200 when the pump device 100 is attached to the controller device 200. Such energy transmission is described in more detail below. In some embodiments, the first power source 345 can be maintained in a storage mode and then switched to an activation mode when the pump device 100 is used to dispense medicine. The storage mode can provide a long shelf life of storage for the first power source 345. For example, when in storage mode, the first power source can retain a substantial portion of its charge for a period of more than six months, more than one year, or more than two years. As shown in FIGS. 11, 13, 18, and 19, the first power source 345 can be equipped with a removable tab 141 that seals the first power source 345 to maintain it in the storage mode. Thus, when the pump device 100 is prepared for usage, the removable tab 141 can be pulled away from the pump housing 110, which switches the first power source into the activation mode. When the first power source 345 is switched to the activation mode, the first power source 345 can dispense electrical energy for a usage period in which the pump device is used. For example, in some embodiments, the first power source 345 can provide electrical energy to other components (e.g., the second power source 245) over a usage period of about one week to about one month (e.g., about two weeks).

The first power source 345 can include a disposable, replaceable, and/or non-rechargable battery (e.g., a zinc-air cell). The first power source 345 can have a large volumetric energy density compared to the second power source 245. For example, the first power source 345 can be a zinc-air cell battery that has a volumetric energy density of greater than about 900 Watt-hours/Liter (Wh/L), about 1000 Wh/L to about 1700 Wh/L, and about 1200 Wh/L to about 1600 Wh/L. Also, the zinc-air cell battery can have a long storage life, as described above. One exemplary zinc-air cell battery is available from Duracell Corporation of Bethel, Conn., which can provide a potential voltage of about 1.1V to about 1.6V (about 1.2V to about 1.4 V, and about 1.3 V in one embodiment), a current output of about 8 mA to about 12 mA (about 10 mA in one embodiment), and a storage capacity of greater than about 600 mA·h (about 650 mA·h in one embodiment). Although described as being disposable and replaceable as being a part of the pump device 100, in some embodiments, the first power source 345 can be individually replaceable from the pump device 100 or from a monolithic infusion pump system.

Referring again to FIG. 15, the control circuitry 240 of the controller device 200 can include a second power source 245, which can be coupled to the power supply board 244 of the control circuitry 240. The second power source 245 can be a rechargeable energy source (e.g., a lithium polymer battery). The second power source 245 can include a high current-output battery that is capable of discharging a brief current burst to power, for example, a drive system of the pump device 100 and can be capable of accepting and storing electrical energy over time (e.g., "trickle charge"). For example, the second power source 245 can be charged with energy supplied from the first power source 345. The hard-wired transmission of electrical energy from the second power source 245 to the drive system 300 can occur through the previously described connectors 118 and 218 (FIGS. 4-5). The second power source 245 can receive electrical energy from a power source housed in the pump device 100 (e.g., the first power source 345), from a plug-in wall charger, from a cable connector (e.g., a USB connection port that is connected to the control circuitry 240), or from another charging device (e.g., a charging cradle).

The second power source 245 can include a high current-output device that is contained inside the controller housing 210. The second power source 245 can be charged over a period of time (e.g., by a first power source 345) and can intermittently deliver high-current bursts to the drive system 300 over brief moments of time. For example, the second power source 245 can include a lithium-polymer battery. The second power source 245 (e.g., lithium polymer battery) disposed in the controller device 200 can have an initial current output that is greater than that of the first power source 345 (e.g., zinc-air cell battery) disposed in the pump device 100, but the first power source 345 can have an energy density that is greater than the second power source 245 (e.g., the lithium polymer battery disposed in the controller device 200 can have a volumetric energy density of less than about 600 Wh/L). In addition, the second power source 245 (e.g., lithium-polymer battery) can be readily rechargeable, which can permit the first power source 345 disposed in the pump device 100 to provide electrical energy to the second power source 245 for purposes of recharging. One exemplary lithium-polymer battery can provide a initial current output of about greater than 80 mA (about 90 mA to about 110 mA, and about 100 mA in one embodiment) and a maximum potential voltage of about 4.0V to 4.4V (about 4.2 V in some embodiments). In other embodiments, it should be understood that the second power source 245 can include a capacitor device capable of being recharged over time and intermittently discharging a current burst to activate the drive system 300. Additional embodiments of the power source 245 can include a combination of batteries and capacitors.

Accordingly, the infusion pump system 10 can have two power sources 345 and 245—one arranged in the disposable pump device 100 and another arranged in the reusable controller device 200—which can permit a user to continually operate the controller device 200 without having to recharge a battery via a plug-in wall charger or other cable. Because the controller device 200 can be reusable with a number of pump devices 100 (e.g., attach the new pump device 100' after the previous pump device 100 is expended and disposed), the second power source 245 in the controller device can be recharged over a period of time, each time when a new pump device 100 is connected thereto. Such a configuration can be advantageous in those embodiments where the pump device 100 is configured to be a disposable, one-time-use device that attaches to a reusable controller device 200. For example, in those embodiments, the "disposable" pump devices 100 recharges the second power source 245 in the "reusable" controller device 200, thereby reducing or possibly eliminating the need for separate recharging of the controller device 200 via a power cord plugged into a wall outlet.

Some embodiments of the controller device 200 can employ a process for maintaining the second power source 245 at or above a threshold charge level when the first power source 345 is electrically connected to the infusion pump system and in a non-depleted state. Based at least in part on this threshold charge level, the infusion pump system can estimate a remaining amount of operation power available to the system. As described below, the second power source 245 can be maintained above the threshold charge level by applying charge to the second power source 245 when the voltage output of the second power source 245 falls below a threshold voltage output. The threshold voltage level can correspond to the threshold charge level. For example, a voltage output of 3.65V can correspond to a charge level of about 80% of the total capacity of the second power source 245, thus by checking the voltage output of the second power source 245 at regular intervals (e.g., every 3 minutes), and setting the threshold voltage level at 3.65V, the second power source 245 can reliably have a charge level above a threshold charge level of 79% of the total capacity. By estimating the remaining amount of operational power based at least in part on the threshold charge level, the system can avoid the need for test charge circuits, which can further drain the second power source.

The controller device 200 can also employ a plurality of techniques (e.g., audio and visual) for notifying the user when an estimated remaining operational power available to the system 10 falls below one or more predetermined levels. In addition, the controller device 200 can employ certain rules to limit the use of certain features of the system 10 when an estimated charge level of the power source 245 falls below one or more predetermined levels or when an estimated amount of operation time available to the system falls below one or more predetermined levels. These rules can limit particular user-controlled functions to assure that there is enough remaining charge to safely operate pump system 10 and dispense the medicine therefrom. In some circumstances, these rules implemented by the controller device 200 can shut down the pump system 10 for the purpose of maintaining a predetermined minimal amount of charge (e.g., a reserve charge) in the power source 245 after the first power source 345 is depleted. This reserve charge can be used to maintain, among other things, the internal memory of the system 10 and the ability of the system 10 to restart based on the application of a recharging source, such as replacing the exhausted pump device 100 with a new pump device 100' (FIGS. 11-12) to provide a new, fully charged first power source 345.

Referring again to FIG. 15, the pump system 10 can include charger controller 247, which can be disposed in the controller device 200. The charger controller 247 can serve as a gatekeeper to operate the charging and discharging of the second power source 245. For example, the charger controller 247 can cause the second power source 245 to output power to the drive system 300, to receive recharging power from the first power source 345, or both. In this embodiment, the charger controller 247 can activate a charging circuit 248 to provide the recharging power. The charging circuit 248 can modify the recharging power from the first power source 345 so as to provide a constant current (e.g., 2.4 mA) to the second power source 245. The charging circuit 248 can be activated to recharge the second power source 245 when the remaining charge in the second power source 245 falls below a lower charge level trigger (e.g., 80% of total capacity) to maintain the second power source 245 at a charge above a threshold charge level (e.g., 79% of total capacity), and the charging circuit 248 can be deactivated to thereby discontinue recharging when the remaining charge in the second power source 245 rises to nearly 100% of total capacity (e.g., about 98% of total capacity). It is noted that various charge level triggers can be used to maintain the charge of the second power source 245 above a threshold charge level used to determine an estimated amount of operation power remaining for the system once the first power source 345 is depleted or disconnected from the system or pump device 100.

In some embodiments, the charger controller 247 can be responsible for monitoring the system 10 power and energy usage and determining the charge remaining in the power source 245. The charge remaining in the second power source 245 can be estimated based on the current output voltage of the second power source 245. An exemplary lithium-polymer battery may have a 4V output voltage which corresponds to a 100% charge level (e.g., the second power source 245 contains 100% of its total charge capacity), while the same lithium-polymer battery producing a 3.65V output voltage may correspond to an 80% charge level (e.g., the second power source 245 contains 80% of its total charge).

In some embodiments, the charger controller 247 can estimate the total energy consumed by the system 10 during a given period of time. In one example, the charger controller 247 can contain predetermined estimates of the amount of power used by specific features (e.g., the drive system 300, the illumination instrument 230, and the like). As the features are utilized, the charger controller 247 can keep a record of when and how long these features are used. To estimate the total energy used, the charger controller 247 can multiply the estimated power usage for each feature by the amount of time a particular feature was used. In some embodiments, the charger controller 247 can include a timer which can perform a count up/down beginning with initiation of the timer. For example, the charger controller 247 can start a timer at thirty minutes and count down to zero. In other situations, the charger controller 247 can start a timer at zero and count up.

Figure 16:
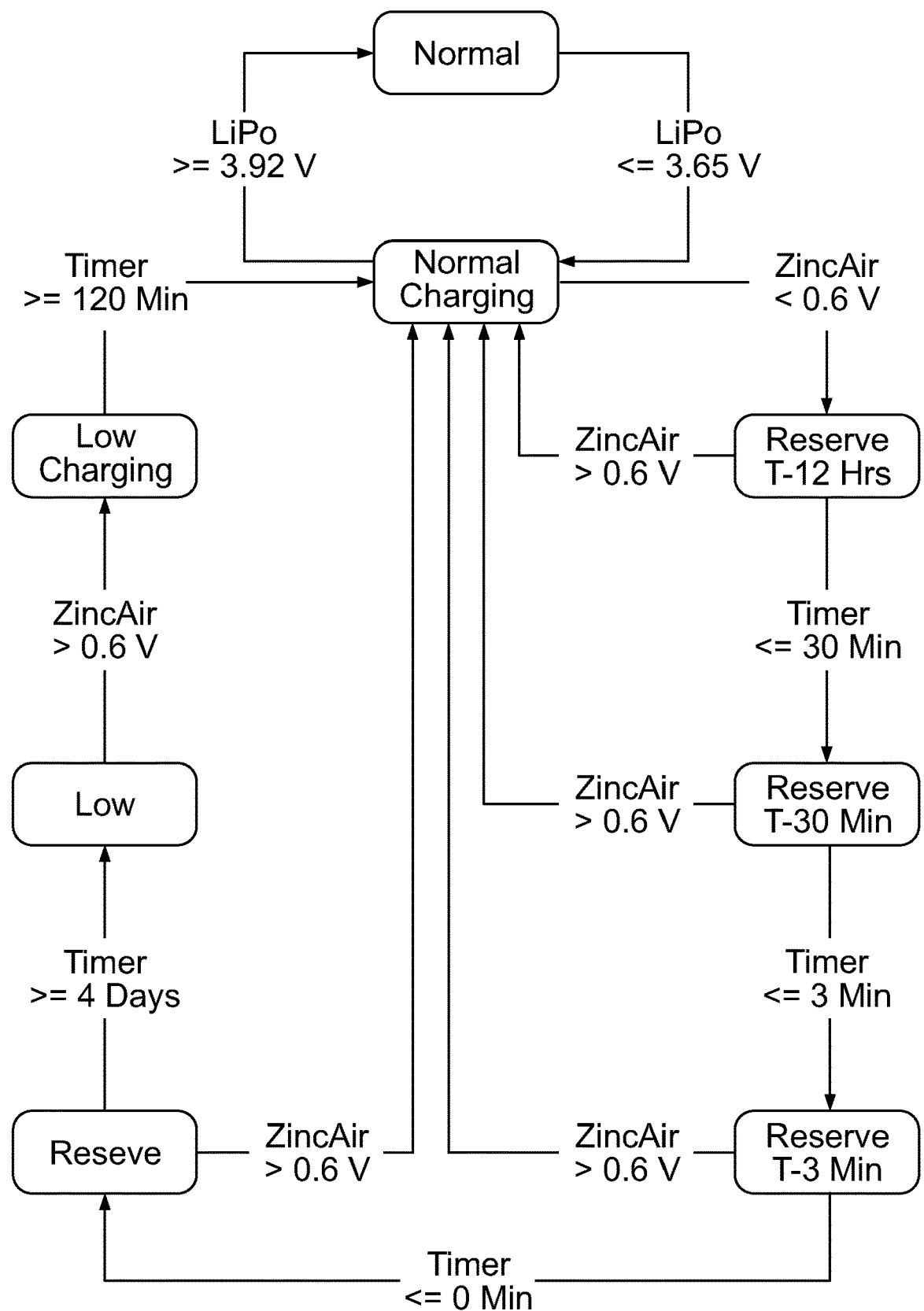
FIG. 16 is a flow chart depicting power states of the infusion pump system.

Referring to FIG. 16, some embodiments of pump system 10 has eight power states that are defined by the first power source 345 and the second power source 245. The "Normal" state can occur when the rechargeable power source 245 is in a fully charged state and requires no charging. In some embodiments, a fully charged state is determined to be when the total charge in the second power source 245 is greater than a threshold charge level (e.g., 79% of the total charge capacity of the second power source 245). Some charge levels can be estimated by the voltage output of the second power source 245 (e.g., the 80% charge level can correspond to the lithium polymer battery 245 having an output voltage of 3.65 V), which can allow the controller to keep the charge level of the second power source 245 above a threshold charge level (e.g., 79%). When the system 10 is in the "Normal" state, all functions and circuits of the system 10 (e.g., pump device 100, drive system 300, user interface 220, illumination instrument 230, and the like) can be available to the user. Additionally, since the power source 245 is adequately charged, no charging is required (e.g., from the first power source 345).

In some embodiments, the second power source 245 can discharge energy during operation of the pump system 10, leading to a lowered output voltage of the power source 245. In some embodiments, the charger controller 247 can monitor the charge remaining in the power source 245 by determining the voltage of the second power source 245 at selected intervals (e.g., about 1 minutes to about 10 minutes, about 2 minutes to about 5 minutes, and in this embodiment about every 3 minutes). The selected interval can determine the relationship between the threshold charge level used to estimate a remaining amount of operational power available and charge levels used to trigger the charging of the second power source 245 with energy from the first power source 345. At such a time when the output voltage of the second power source 245 falls below a threshold voltage output (e.g., 80% of the total charge capacity or about 3.65 V in this embodiment), the charger controller 247 can transition the system 10 to the "Normal Charging" state. For example, if the controller determines a voltage output every minute, when a voltage of less than 3.65V triggers the recharging of the second power source 245, then this can correspond to a threshold charge level of about 79.5% of total capacity that would be used to determine the remaining amount of operation power. In other examples, a voltage detection interval of 10 minutes, with a voltage of less than 3.65V triggering the recharging of the second power source 245, can correspond to a threshold charge level of about 78%.

As shown in FIG. 16, when in the "Normal Charging" state, the controller device 200 operates to determine the ability of the system 10 to charge the power source 245. For example, in this embodiment, the charger controller 247 can determine the charge remaining in the first power source 345. If the first power source 345 is capable of supplying energy to the second power source 245 (e.g., if the Zinc-Air battery in this embodiment has a voltage greater than 0.6 V), then the second power source 245 can be charged from the first power source 345. A voltage output of first power source 345 can indicate whether the first power source 345 is in a depleted or non-depleted state (e.g., a voltage output above 0.6 V can indicate a non-depleted zinc-air battery, which a voltage output of below 0.6 V can indicate a depleted zinc-air battery). Charging of the second power source 245 from the first power source 345 can continue until a predetermined condition occurs. For example, the second power source 245 can receive energy until it reaches a upper charge level (e.g., 98% of the total charge capacity of the second power source 245). In some embodiments, the current level of charge can be estimated by the voltage output of the second power source 245 (e.g., 98% of total charge capacity can correspond to the lithium polymer battery having an output voltage of 3.92 V in this embodiment). As shown in FIG. 16, when the second power source 245 reaches a upper voltage output trigger (e.g., 98% of total charge capacity or 3.92 V in this embodiment), the controller 247 can transition the system 10 to the "Normal" state.

In some circumstances, the charging of the second power source 245 can continue until such a time as the first power source 345 becomes depleted (e.g., the Zinc-Air battery in this embodiment falls below a predetermined voltage, such as 0.6 V). Although a depleted first power source 345 may retain some charge, the remaining charge is not sufficient to continue to efficiently and significantly charge the second power source 245 (e.g., a voltage output of 0.6 V for a zinc-air battery indicates that the zinc-air cell only retains a very small percentage of its initial charge and/or is unable to efficiently recharge the first power source 245, and is therefore depleted). When the voltage output of the first power source 345 indicates that the first power source 345 is depleted, the system 10 can be transferred to a "Reserve T-12 Hr" state, which can indicate that the first power source 345 is depleted and that the pump system 10 can be operated with the remaining power of the second power source 245. In some embodiments, the system can be configured such that once the first power source 345 has been depleted, the second power source 245 can supply full power to the system 10 for at least a predetermined amount of time. As shown, the predetermined amount of time is about 12 hours. In other embodiments, the predetermined amount of time can about 4 hours or greater, about 8 hours to about 24 hours, or about 12 hours or greater. The predetermined amount of time (e.g., 12 hours in this embodiment) can be based on the total energy in the second power source 245 when the second power source 245 is at the threshold charge level (e.g., the total energy at 79% of capacity) and an estimate of high battery usage of a user. In some embodiments, when the system 10 is in the "Reserve T-12 Hr" state, all functions and circuits of the system 10 (e.g., pump device 100, drive system 300, user interface 220, illumination instrument 230, and the like) can be available to the user. In other embodiments, the controller device 200 may operate to restrict some high-energy features (e.g., the illumination instrument 230).

As previously described, the remaining time can be estimated from, among other factors, the threshold charge level of the second power source 245 without the need for additional circuitry for sampling battery charge or algorithms for estimating remaining power based on output voltage. For many types of batteries, including some lithium polymer batteries, an estimation of charge level from the voltage output of the battery may only be accurate when the battery has a charge level near total capacity or a charge level when the battery is nearly depleted. Maintaining the second power source 245 at a charge level above the threshold charge level while the first power source 345 is in a non-depleted state can ensure that the second power source 245 has at least the threshold charge remaining at the time when the first power source 345 enters a depleted state. Furthermore, the threshold charge level can be selected to ensure that an algorithm using the voltage output can accurately predict the charge level of the second power source 245.

In some embodiments, the threshold charge level can correspond to an amount of medicine dispensing time based on a high power consumption estimate (e.g., usage of the pump system 10 in a manner that consumes power at a higher than normal rate). For example, the threshold charge level can be set on a second power source 245 of sufficient capacity to ensure at least 12 hours of medicine dispensing time remaining once the first power source 345 becomes depleted. In some embodiments, a timer in the control circuitry 240 (FIG. 15) can begin at 12 hours once the first power source 345 is depleted and count down towards zero. Once the timer reaches zero, the system 10 can be, for example, transitioned into another state. Such embodiments do not necessarily require additional charge-detecting circuitry that would draw upon the remaining power in order to determine when the system 10 is running low on power.

In another example, an initial estimate of time (e.g., 12 hours) can be made, but updated based on, for example, the total energy remaining in the second power source 245 at the threshold charge level minus a safety factor and the usage since transitioning to the "Reserve T-12 Hr" stage. In some embodiments, this usage can be an estimate based on the total usage of the drive system 300, the total usage (e.g., in seconds) of the user interface 220, and/or the total usage (e.g., in seconds) of the illumination instrument 230. For example, if the total usable energy (total power at the threshold charge level minus safety factor) of a fully charged power source 245 is estimated to be 20 mAh, the system 10 has been in the "Reserve T-12 Hr" state for 2 hours, and the estimated usage during that time was 2.50 mAh, then the estimated time remaining can be determined to be 14 hours ((20−2.5) mAh*(2 h/2.5 mAh)). In another example, if a total usable charge (total power at the threshold charge level minus safety factor) of a fully charged power source 245 is estimated to be 20 mAh, the system 10 has been in the "Reserve T-12 Hr" state for 1 hour, and the estimated usage during that time is 2 mAh, then the estimated time remaining can be 9 hours ((20−2) mAh*(1 h/2 mAh)).

When the system 10 is in the "Reserve T-12 Hr" state, there can be a relatively limited amount of time (e.g., 12 hours) remaining where all features of the system 10 are available to the user. Due to this relatively limited amount of time, it can be advantageous to alert the user, notifying him/her that steps should be taken to ensure the uninterrupted use of the system 10. This notification, in some embodiments, could include an alert message displayed on the display device 222 indicating that the user only has a certain amount of time remaining (e.g., as shown in FIG. 1). In some embodiments, the notification could also suggest that the user connect the pump system 10 to an external power source, such as an outlet, or have a replacement pump device available. The alert can be constant or intermittent. The alert could instead be an audible alert or an sound could be used in combination with a visual alert. The alert could also alternate with the visual contents of the display device 222 (e.g., as shown in FIG. 2). Additional forms of notification could include a light (e.g., the illumination device 230) that flashes, an audible beep that occurs, a backlight or display that flashes and/or changes color, for example every half hour or every hour, to alert the user to check the display device 222 for the alert message. In some embodiments, the backlight or display could change color when the system enters the "Reserve T-12 Hr" state (e.g., from green when the first power source 345 is connected and non-depleted to red when the first power source 345 is depleted or disconnected).

Still referring to FIG. 16, when in the "Reserve T-12 Hr" state, all functions and circuits of the system 10 (e.g., pump device 100, drive system 300, user interface 220, illumination instrument 230, and the like) can be available to the user. Various events or conditions can occur that can cause the system 10 to transition out of the "Reserve T-12 Hr" state. One condition can occur when, for example, the existing pump device 100 is replaced with a new pump device 100' including a fully charged first power source 345 (FIGS. 11-12). When a fully charged first power source 345, or at least non-depleted first power source (e.g., a Zinc-air cell having a voltage output of greater than 0.6 V), is detected by the control circuitry 240, the system 10 can transition into the "Normal Charging" state. In some embodiments, the system can check the voltage output of the first power source 345 when a pump device is attached or reattached to the controller device. In some embodiments, the controller device 200 can store information indicating that the first power source 345 for a particular pump device 100 is depleted to prevent the need to further check whether the first power source 345 is depleted or non-depleted. Another transition condition can occur when the control circuitry 240 determines that there is only 30 minutes of battery life remaining in the power source 245 (e.g., by a countdown timer, an estimate of remaining charge based on usage while in the "Reserve T-12 Hr" state, or the like), at which time the system 10 can transition into the "Reserve T-30" state.

When in the "Reserve T-30" state, all functions and circuits of the system 10 (e.g., pump device 100, drive system 300, user interface 220, illumination instrument 230, and the like) can be available to the user. However, in some embodiments, certain features may become unavailable to the user when in the "Reserve T-30" state. At the time when the system 10 transitions into the "Reserve T-30" state, a 30 minute countdown timer can be initiated and the user can be alerted via the display device 222 (e.g., an alert message indicating the number of minutes remaining) and an intermittent audible beep, until acknowledged (e.g., by pressing one of the user-selectable buttons). The alert can also direct the user to supply an additional power by, for example, replacing the pump device 100 or by plugging the pump system 10 into an outlet. The system 10 can remain in this state until a condition occurs that causes the system 10 to transition to a different state. For example, the system 10 can transition to a different state when the existing pump device 100 is replaced with a new pump device 100' with a fully charged, or at least non-depleted, first power source 345 (FIGS. 11-12). When a non-depleted first power source 345 is detected by the control circuitry 240, the system 10 can transition into the "Normal Charging" state. The system 10 can transition to a different state when the control circuitry 240 determines that there is only 3 minutes of battery life remaining in the power source 245 (e.g., the countdown timer started in the "Reserve T-30" state reaches 3 minutes), at which time the system 10 can transition into the "Reserve T-3" state.

Still referring to FIG. 16, at the time when the system 10 transitions into the "Reserve T-3" state, the countdown timer started in the "Reserve T-30" state can continue and the user can be alerted via the display device 222 (e.g., a flashing message indicating the number of minutes and seconds remaining) and/or an audible alarm (e.g., a constant audible beep), until acknowledged (e.g., by pressing one of the user-selectable buttons). While in the "Reserve T-3" state, all functions and circuits of the system 10 (e.g., pump device 100, drive system 300, user interface 220, illumination instrument 230, and the like) can be available to the user, but for less than 3 minutes. The system 10 can remain in this state until a condition occurs that causes the system 10 to transition to a different state. For example, the system can transition to a different state when the existing pump device 100 is replaced with a new pump device 100' (FIGS. 11-12) with a fully charged, or at least non-depleted, first power source 345. When a non-depleted power source 345 is detected by the control circuitry 240, the system 10 can transition into the "Normal Charging" state. The system 10 can transition to a different state when the control circuitry 240 determines that there is little or no battery life remaining in the power source 245 (e.g., the countdown timer started in the "Reserve T-30" state reaches zero), at which time the system 10 can transition into the "Reserve" state.

The system 10 can transition into the "Reserve" state when the countdown timer reaches zero, indicating that there is no longer enough total power to both safely operate the system 10 and to maintain the system 10 in the "Reserve" state for a predetermined period of reserve time (e.g., about 1 day to about 7 days, and about 4 days in this embodiment). In some embodiments, while in the "Reserve" state, the controller device 200 can restrict usage of features such as the drive system 300 and the illumination instrument 230 due to power issues, but other features such as the display device 222 can remain available to the user (e.g., allowing the user to review the status and logbook screens).

The controller device 200 can maintain the system 10 in the "Reserve" state for a particular amount of reserve time (e.g., about 1 day to about 7 days, and about 4 days in this embodiment) before transitioning the system 10 to the "Low" state. In some embodiments, while in the reserve state, no pump or user functions are allowed. For example, in response to a user pressing any of the user-selectable buttons, the system 10 can return a message (e.g., "Off—No Power, Pump Stopped") on the display device 222, while not performing the task usually associated with the button that was pressed. The system 10 can remain in this state until a condition occurs that causes the system 10 to transition to a different state. For example, the system 10 can transition to a different state when the existing pump device 100 is replaced with a new pump device 100' with a fully charged first power source 345 (FIGS. 11-12). When a fully charged, or non-depleted, first power source 345 is detected by the control circuitry 240, the system 10 can transition into the "Normal Charging" state. The system 10 can transition to a different state after a predetermined amount of time (e.g., 4 days) or when the control circuitry 240 determines that the voltage in the power source 245 has fallen below a predetermined minimum (e.g., 3.1 V), at which time the system 10 can transition into the "Low" state.

Still referring to FIG. 16, the system 10 can transition into the "Low" or "Deep Sleep" state when the power source 245 is almost completely depleted (e.g., after 4 days in the "Reserve" state or when the voltage of the power source 245 falls below 3.1 V). For example, while in this state, many features of the system 10 can be unavailable to the user (e.g., the drive system 300, and/or reviewing the logbook screen). In some embodiments, the only event that causes a response is the insertion of a new pump body with a charged power source 345 at which time the system 10 transitions into the "Low Charging" state. Due to the low power consumption of the "Low" state, the system 10 can remain in this state for an extended (e.g., 2 week) period of time. For example, a lithium polymer battery can have a protection circuit that disconnects the lithium polymer battery when the voltage output falls below a predetermined level (e.g., 2.3 V).

In some embodiments, once in the "Low Charging" state, the user can be notified (e.g., with a "Charging" message on the display device 222) and a timer is initiated (e.g., beginning at zero and counting up). For example, while in the "Low Charging" state, many features of the system 10 can be unavailable to the user (e.g., the drive system 300, and/or the illumination device 230). In some embodiments, the system can be in the "Low Charging" state for between 30 minutes and 2 hours before the first power source 245 has sufficient charge allow for return to the "Normal Charging" state and thus normal operation. In some embodiment, a timer can begin once a non-depleted first power source 345 is detected and the system returned to "Normal Charging" when the timer reaches 120 minutes, indicating that a sufficient charge is present in the power source 245, the system 10 transitions to the "Normal Charging" state.

While eight power states of the system 10 were described herein, there can exist other power states not depicted in FIG. 16. In some embodiments, a ninth power state (e.g., "External Charging") can exist. The system 10 can transition to this state when connected to an external charging apparatus (e.g., when the system 10 is connected to a charging cradle, plugged into a wall outlet, or connected to a computer via a USB cable). While connected to the external charging apparatus, the controller 247 may disable the charging circuit 248, allowing charging of the second power source 245 to be managed by the external charging device. In some embodiments, the controller 247 can manage the charging of the second power source 245 from an external apparatus either through the use of the charging circuit 248, or through an additional charging circuit dedicated for use with an external charging apparatus.

Figure 17:
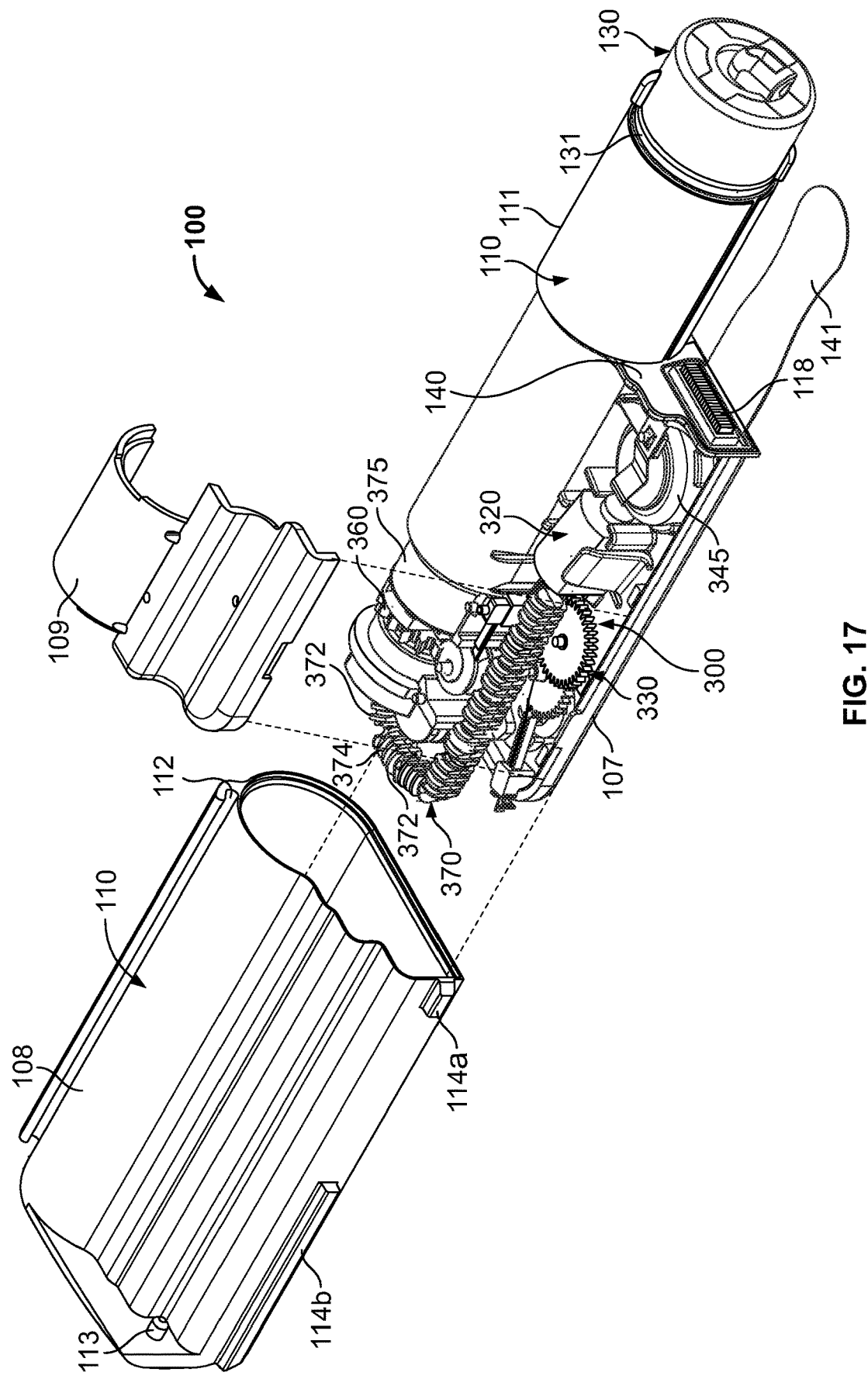
FIG. 17 is an exploded perspective view of a pump device for an infusion pump system, in accordance with some embodiments.
Figure 18:
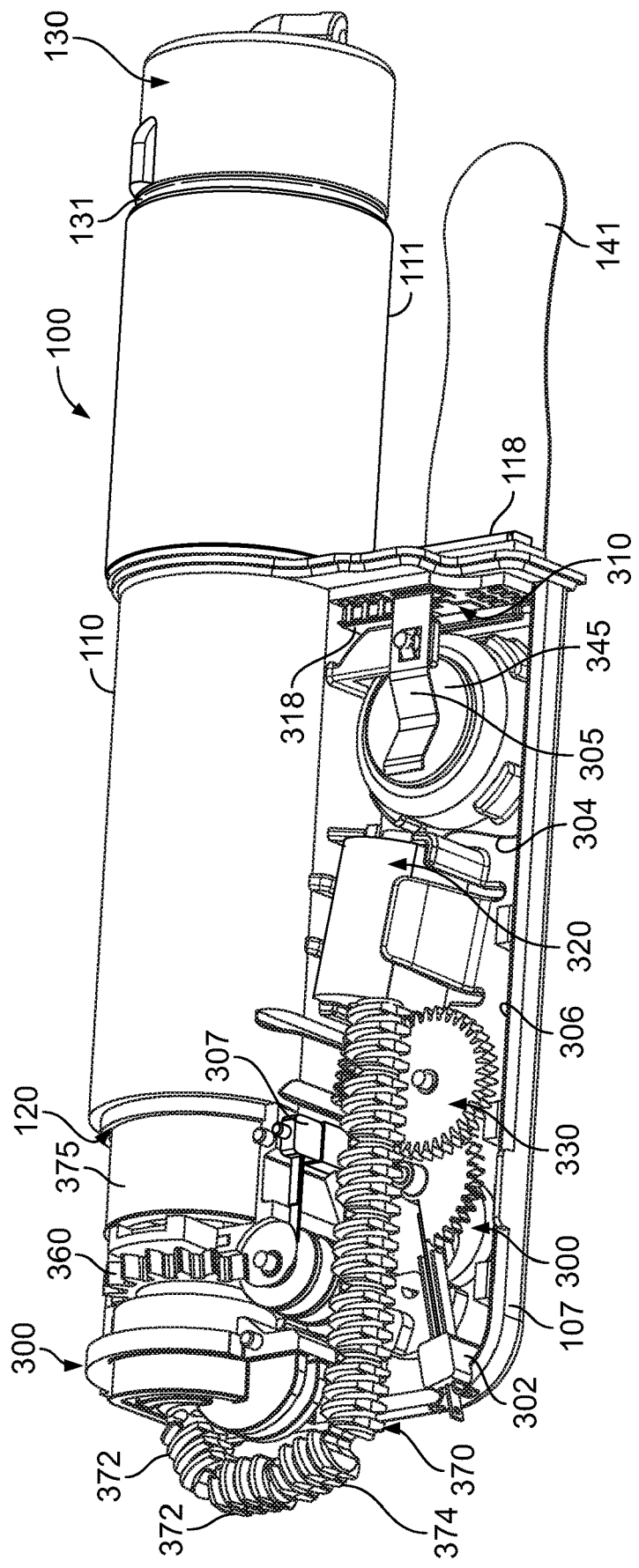
FIG. 18 is a perspective view of a portion of the pump device of FIG. 17.
Figure 19:
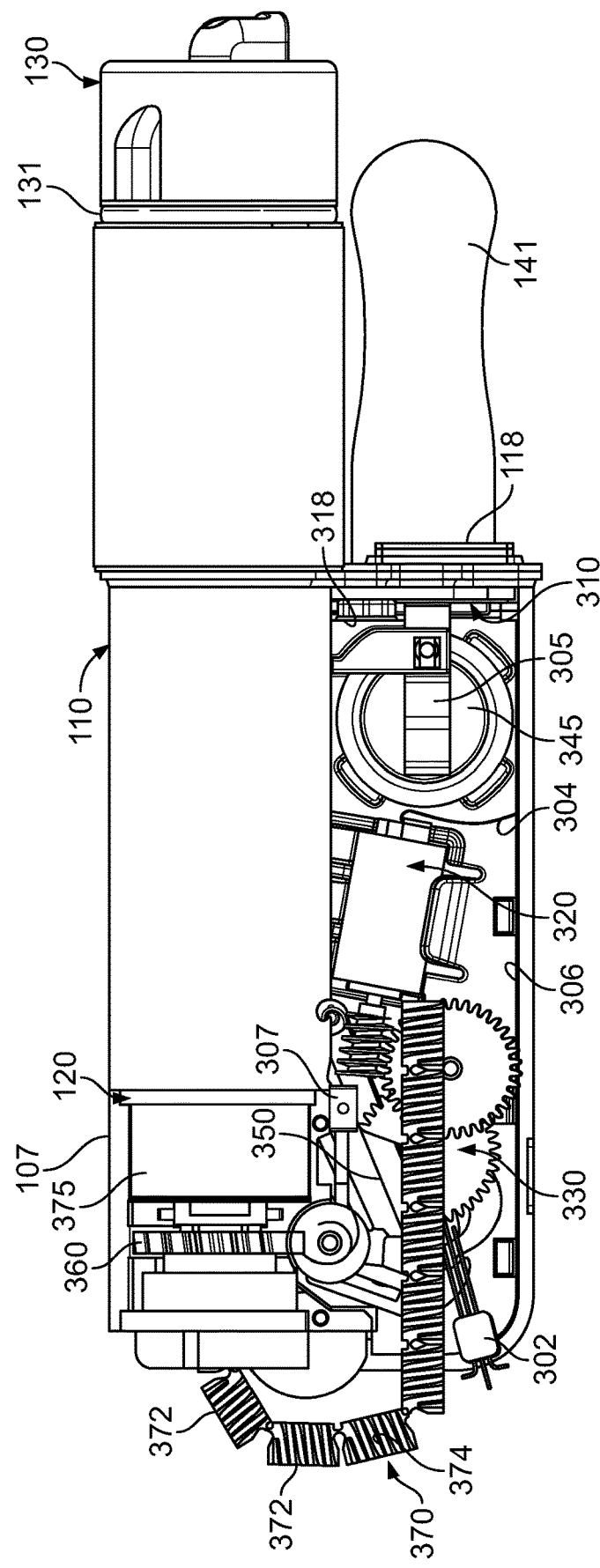
FIG. 19 is a top view of a portion of the pump device of FIG. 17.

Referring now to FIGS. 17-19, the pump device 100 can include the drive system 300 that is controlled by the removable controller device 200 (FIGS. 1-5). Accordingly, the drive system 300 can accurately and incrementally dispense fluid from the pump device 100 in a controlled manner. The drive system 300 can include a flexible piston rod 370 that can be incrementally advanced toward the medicine cartridge 120 so as to dispense the medicine from the pump device 100. At least a portion of the drive system 300 can be mounted, to the pump housing 110. In some embodiments, the pump housing 110 can include a chassis 107, a shell portion 108, and a cover mount 109. The shell portion 108 can be used to cover at least a portion of the drive system 300. For example, the shell 108 can include an inner curved surface against which a curved section of a piston rod 370 rests. The cover mount 109 may be assembled to the chassis 107 of the pump housing 110 to secure some components of the drive system 300 in position between the cover mount 109 and the chassis 107. When the cover mount 109 is assembled into place, the "unused" or retracted portion of the piston rod 370 can rest in a channel defined in the top of the cover mount 109. The shell portion 108 can slide over the cover mount 109 and join with the chassis 107 to form the assembled pump housing 110.

Some embodiments of the drive system 300 can include a battery powered actuator (e.g., reversible motor 320 or the like) that resets a ratchet mechanism 330, a spring device 350 (FIG. 20) that provides the driving force to the ratchet mechanism 330, and a drive wheel 360 that is rotated by the ratchet mechanism 330 to advance the flexible piston rod 370 toward the medicine cartridge 120. The operation of the drive system 300 is described in more detail below in connection with FIGS. 20-23.

As shown in FIGS. 18-19, the pump device 100 can include one or more motion detectors coupled with the drive system 300 to provide feedback regarding the operation of the drive system 300. For example, the pump device 100 can include a first motion detector 302 configured as a limit switch that detects when a portion of the ratchet mechanism has reached the limit of its travel and must thereafter stop movement or reverse direction. The operation of the limit switch 302 is described in more detail below in connection with FIGS. 20-23. In another example, the pump device 100 can include a second motion detector 307 in the form of a mechanical error switch that indicates whether components of the drive system 300 completed the desired motion for each drive cycle. The operation of the mechanical error switch 307 is described in more detail below in connection with FIGS. 20-23.

Referring to FIGS. 18-19, the pump device 100 can include a connector circuit 310 to facilitate the transfer of signals to and from the electrical connector 118. As previously described, the electrical connector 118 of the pump device 100 can mate with the connector 218 (FIG. 4) of the controller device 200 so that electrical communication can occur between the pump device 100 and the controller device 200. The connector circuit 310 can include a generally non-complex circuit 310 that does not include a processor or other relatively high-cost components. In some embodiments, the connector circuit 310 can operate as a passageway for the control signals (from the control circuitry 240 (FIG. 15) of the controller device 200) to transmit to the drive system 300 (e.g., to the actuator 320). For example, the reversible motor 320 may be connected to the connector circuit 310 via one or more wires 304. The connector circuit 310 can also operate as a passageway for the electrical power from the first battery 345 (FIG. 19) to pass to the controller device 200 for recharging of the second battery 245 (FIG. 15). For example, the first battery 345 can be connected to the connector circuit 310 via one or more power contacts 305. Furthermore, the connector circuit 310 can operate as a passageway for feedback signals (e.g., from the motion detectors 302 and 307) to transmit to the control circuitry 240 (FIG. 15) of the controller device 200. For example, the limit switch 302 can be connected to the connector circuit 310 via one or more wires 306 (the one or more wires connecting the mechanical error switch 307 to the connector circuit 310 are not shown in FIGS. 18-19).

The connector circuit 310 in the pump device 100 can include a memory device 318 that can store data regarding the pump device 100 and its operational history. For example, the memory device 318 of the connector circuit 310 can include a flash memory chip that is configured to store data such as: a unique serial number designated for the pump device 100, a manufacturer identifier code, and a drive cycle counter. The unique serial number designated for the pump device 100 and the manufacturer identifier code may be useful pieces of quality control information that remains with the pump device 100 throughout its shelf-life and operational life. If, for example, a manufacturing error is identified for a particular pump device 100, the unique serial number and the manufacturer identifier code (e.g., a lot code) can be used to promptly identify the manufacturing location and/or manufacturing lot.

Because the flexible piston rod 370 can be adjustable from a curved shape to a noncurved shape, the overall length of the pump device can be reduced in some embodiments. For example, in a typical infusion pump that houses a straight and rigid rod, the typical infusion pump requires a package or housing having a linear dimension sufficient to accommodate the length of the rigid piston rod when it is at its limit of travel in which it is fully withdrawn from the container or cylinder. The pump device 100 incorporating the flexible piston rod 370 can require less space than a similar device that houses a non-flexible, rigid rod.

Referring now in more detail to the components of the drive system 300 depicted in FIGS. 20-23, the electrically powered actuator can be in the form of the motor 320 having a rotatable output shaft 321. In some embodiments, the motor 320 can be reversible; it can receive signals that cause the output shaft 321 to rotate in a first rotational direction or in a second, opposite rotational direction. One example of a suitable motor 320 is a coreless DC motor with reversible rotation capabilities. As previously described, the operation of the motor 320 can be controlled by the removable controller device 200 (FIGS. 1-5) via electrical signals communicated through the mating electrical connectors 118 and 218 (FIGS. 4-5).

Still referring to FIGS. 20-23, a gear system 322 can be coupled to the motor 320 so that actuation by the motor 320 causes a pusher arm 325 to act upon the ratchet mechanism 330 or to decouple from the ratchet mechanism 330. In some embodiments, the gear system 322 can include a worm gear 323 and a gear reduction assembly comprising spur gears 324a, 324b, and 324c. As described in more detail below, one of the spur gears (e.g., segmented gear 324c) can engage the limit switch 302 when it reaches the opposite ends of its reciprocating motion, thereby indicating that the motor 320 should reverse its rotational direction or stop rotating.

The pusher arm 325 can be pivotably coupled to the gear 324c so that partial rotation of the gear 324c causes the pusher arm to reciprocate within a guide slot 328. The guide slot 328 can be formed in the body of the chassis 307 (FIGS. 17-19) of the pump housing. The pusher arm 325 can have a slider pin 326 that fits into the guide slot 328 are reciprocates therein.

Accordingly, rotation of the motor 320 in a first direction can be translated into an advancement force to the pusher arm 325. The advancement force on the pusher arm 325 is applied to a pawl member 335, which (in some embodiments) causes the pawl member 335 to pivot to a reset position. In addition, rotation of the motor 320 in a second direction can be translated into an retraction force to the pusher arm 325, which can cause the pusher arm 325 to be separated from the pawl member 335 during the drive step (refer to FIG. 23). As such, the motor 320, the gear system 322, and the pusher arm 325 can collectively operate as an actuator assembly that provides a reliable and consistent adjustment of the ratchet mechanism 330 during a reset step (refer to FIG. 22). Moreover, this actuator assembly (e.g., the motor 320, the gear system 322, and the pusher arm 325) can be activated to separate from the pawl member 335, thereby permitting the motor 320 to decouple from the ratchet mechanism 330 during a drive step (refer to FIG. 23).

Figure 20:
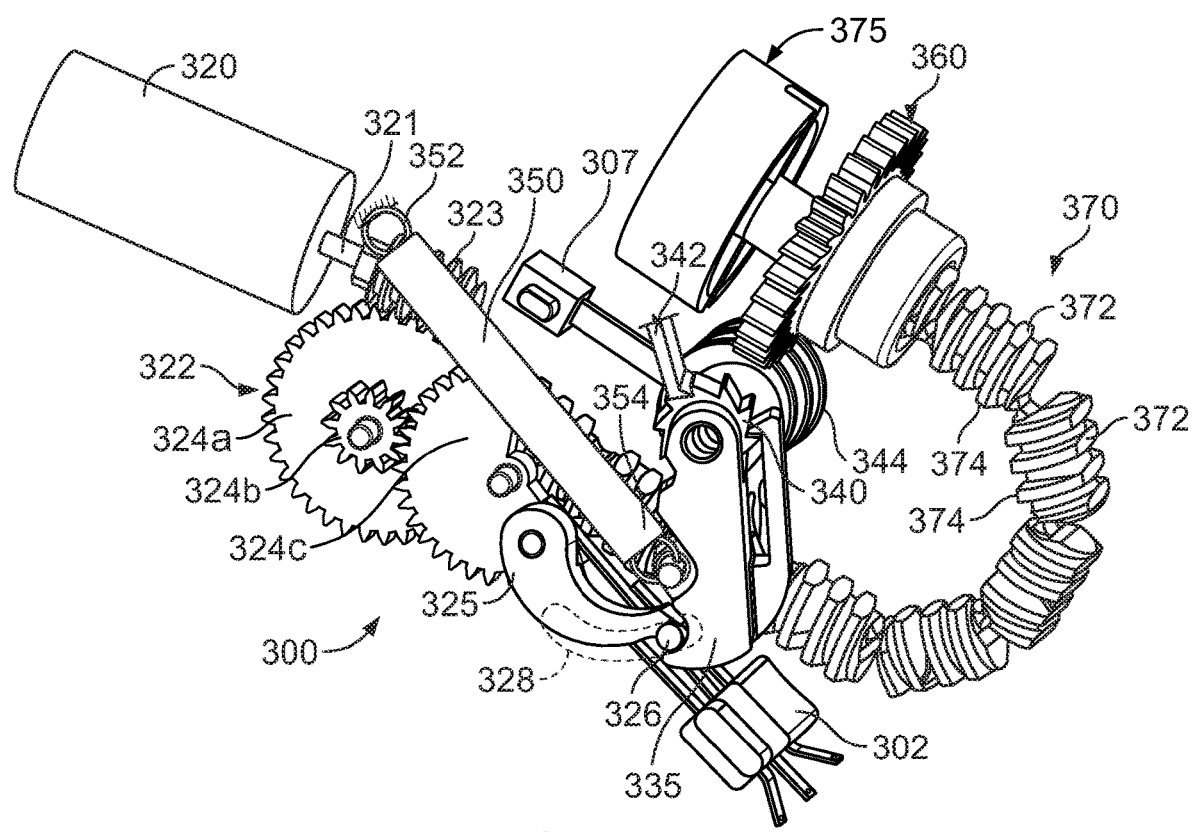
FIGS. 20-23 are perspective views of a portion of a drive system for the pump device of FIG. 17.

Referring to FIG. 20, the motion path of the pusher arm 325 can be configured to provide an efficient mechanical advantage orientation during the desired motion of the adjustable pawl member 335. In some embodiments, the pusher arm 325 can be directed by the guide slot 328 formed in an interior surface of the pump housing 110. The pusher arm 325 can include the slider pin 326 that is received within the guide slot 328 during assembly of the pump device 100. The portion of the pusher arm 325 proximate the slider pin 326 can abut against the pawl member 335 when the pusher arm 325 is advanced. As such, when a first end of the pusher arm 325 is moved by the gear 324c, a second end of the pusher arm (proximate the slider pin 326) can be directed by the guide slot 328. The orientation of the pusher arm 325 relative to the guide slot 328 can be configured to provide an efficient mechanical advantage for the pushing force applied by the pusher arm 325 during the desired motion of the adjustable pawl member 335.

Still referring to FIG. 20, the ratchet mechanism 330 can include the pawl member 335 and a ratchet body 340, which, in the embodiment shown, is a ratchet wheel having a number of teeth along its circumferential surface. In some embodiments, the ratchet wheel 340 can be coupled with a worm gear 344, and incremental rotation of the ratchet wheel 340 can cause rotation of a drive wheel 360 (due to engagement with the worm gear 344). The pawl member 335 can be adjustable between a reset position (refer to FIG. 22) and a forward position (refer to FIG. 23). For example, during the reset step, the motor 320 can be activated to advance the pusher arm 325 (guided by the guide slot 328), and the pusher arm 325 can apply a pushing force that adjusts the pawl member 335 to the reset position in which the pawl member 335 grabs a new tooth of the ratchet wheel 340 (refer to FIG. 22). In some embodiments, the adjustable pawl member 335 can be pivotably coupled to about the axis of rotation for the ratchet wheel 340 and the worm gear 344.

Figure 21:
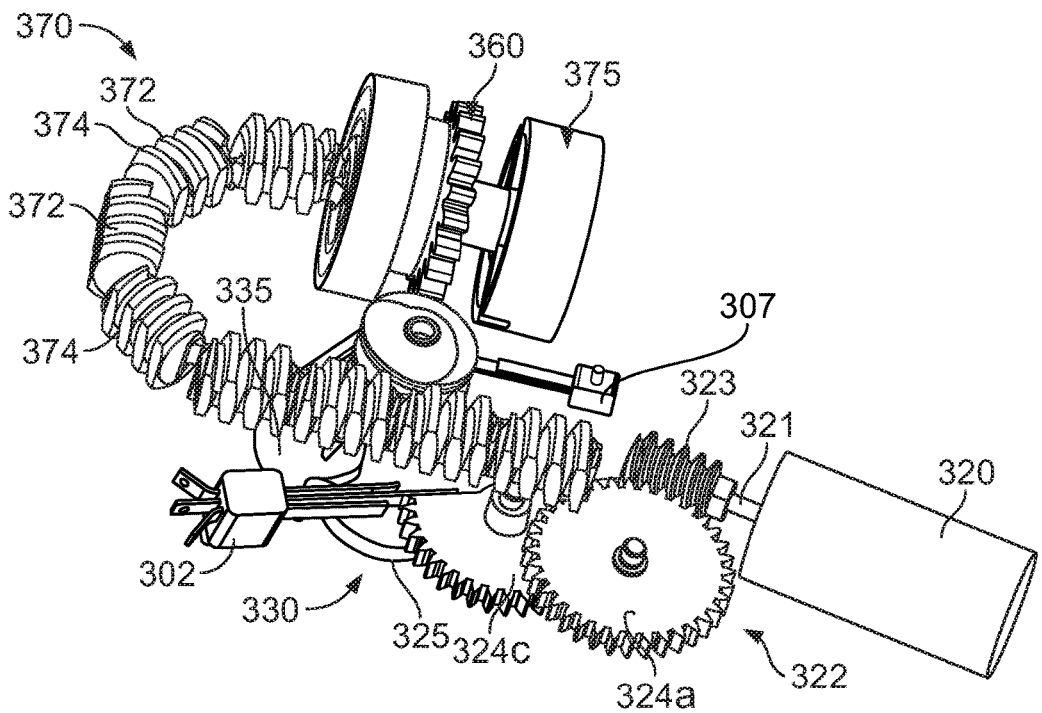
Figure 22:
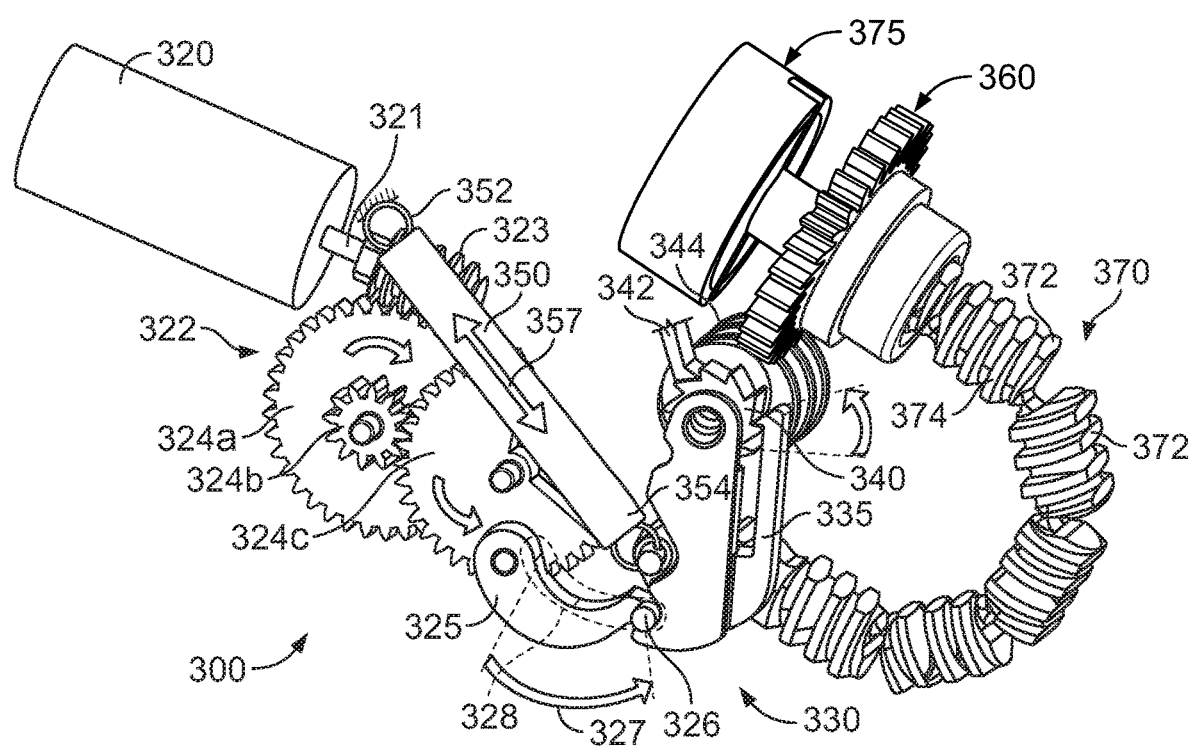
Figure 23:
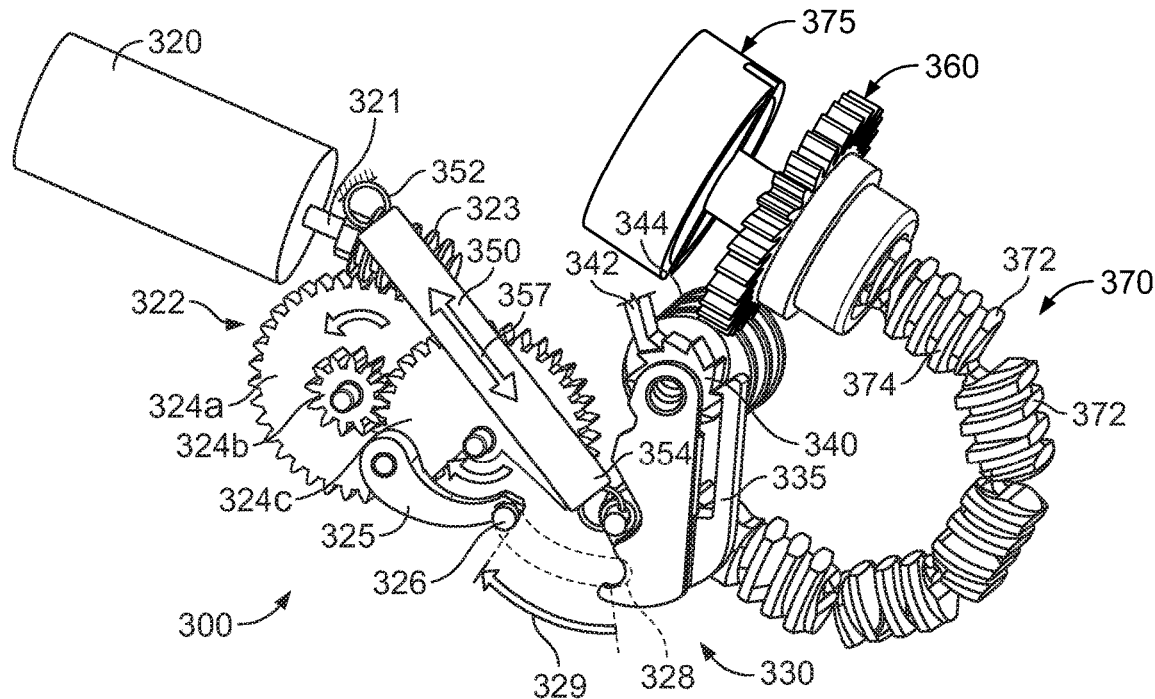

A spring device 350 can be coupled to the pawl member 335 so as to urge the pawl member 335 toward the forward position (refer to FIG. 23). In some embodiments, the spring device 350 can be in the form of a coil spring that is fixed to the pump housing 110 (not shown in FIGS. 20-23) at a first end portion 352 and that is engaged with the pawl member 335 at a second end portion 354. Thus, as shown in FIG. 22, when the pawl member 335 is adjusted to the reset position, the spring device 350 is in tension and stores potential energy that urges the pawl member 335 to return to the forward position (refer to FIG. 23) and thereby drive the ratchet wheel 340 in a forward rotational direction.

In some embodiments, a locking pawl 342 can be used to prevent the ratchet wheel 340 from reverse motion. The locking pawl 342 can flex or otherwise adjust to permit the incremental forward rotation of the ratchet wheel 340. As such, the adjustable pawl member 335 can adjust from the forward position to the reset position to engage a new tooth of the ratchet wheel 340 while the ratchet wheel 340 remains in position due to the locking pawl 342.

Still referring to FIG. 20, in some embodiments, the ratchet wheel 340 can be integrally formed with the worm gear 344 so that the incremental rotation of the ratchet wheel 340 is translated to the worm gear 344. Such rotation of the worm gear 344 can cause rotation of the drive wheel 360. The drive wheel 360 can include a central aperture having an internal thread pattern therein (not shown in FIG. 20), which mates is an external thread pattern 374 on the rod segments 372. Thus, the incremental motion provided by the ratchet mechanism 330, the pusher arm 325, and the motor 320 can cause the drive wheel 360 to incrementally rotate, which in turn translates to a longitudinal advancement of the flexible piston rod 370.

Accordingly, in some embodiments, the piston rod 370 can undergo only forward or positive longitudinal displacement as a result of drive system 300. For example, the drive system 300 can substantially hinder the piston rod 370 from retracting or "backing up" in response to fluid pressure in the medicine cartridge 120 or other reversal forces. In such circumstances, the flexible piston rod 370 can be retracted only upon manual disassembly of the pump device 100 (e.g., to disengage the drive gear 360 or the ratchet mechanism 330). In those embodiments in which the pump device 100 is intended to be disposable and non-reusable, the non-retractable piston rod configuration can facilitate a "one time use" disposable pump device by hindering attempts to insert a new medicine cartridge 120 in a previously used pump device 100. Such a configuration can thereby reducing the likelihood of failure due to non-intended repeated use of the disposable pump device 100.

Referring again to FIGS. 20-21, the pump device can include two or more motion detectors 302 and 307. The first motion detector 302 can include a limit switch that is activated when the segmented gear 324c of the gear system 320 reaches the ends of its reciprocating travel path. The second motion detector 307 can include a mechanical error switch that is activated when the worm gear 344 is incrementally rotated with each drive cycle. For example, as shown in FIG. 21, mechanical error switch 307 can include a first arm 308a that is arranged adjacent to a second arm 308b. The first arm 308a can have a longer length so that it can be engaged by the threads of the worm gear 344. Accordingly, when the drive system 300 operates to incrementally rotate the worm gear 344, the first arm 308a can be temporarily flexed into contact with the second arm 308b. This temporary contact can signal to the controller device 200 that the ratchet mechanism 330 and spring 350 successfully translated the drive energy to rotate the worm gear 344 (which rotates the drive gear 360 and thereby advances the piston rod 370).

As described in greater detail previously in connection with FIGS. 20-23, the drive system 300 can include the reversible motor 320 which operates a gear system 322 that can cause a pusher arm 325 to act upon a ratchet mechanism 330 and a spring device 350. When rotating in one direction, the motor 322 (acting through components such as the gear system 322, the pusher arm 325, the ratchet mechanism 330, and the like) can encourage extension and thus store potential energy in the spring device 350, causing the ratchet mechanism to advance to or "grab" a new tooth on the ratchet body 340. When the motor 322 reverses direction it can decouple (described previously in greater detail in connection with FIG. 23) from components such as the spring device 350 and the ratchet mechanism 330. Once decoupled, the potential energy in the spring device 350 can be utilized to rotate the ratchet body 340, thus causing the plunger engagement device 375 to advance, which in turn can cause medicine to be infused.

Figure 24:
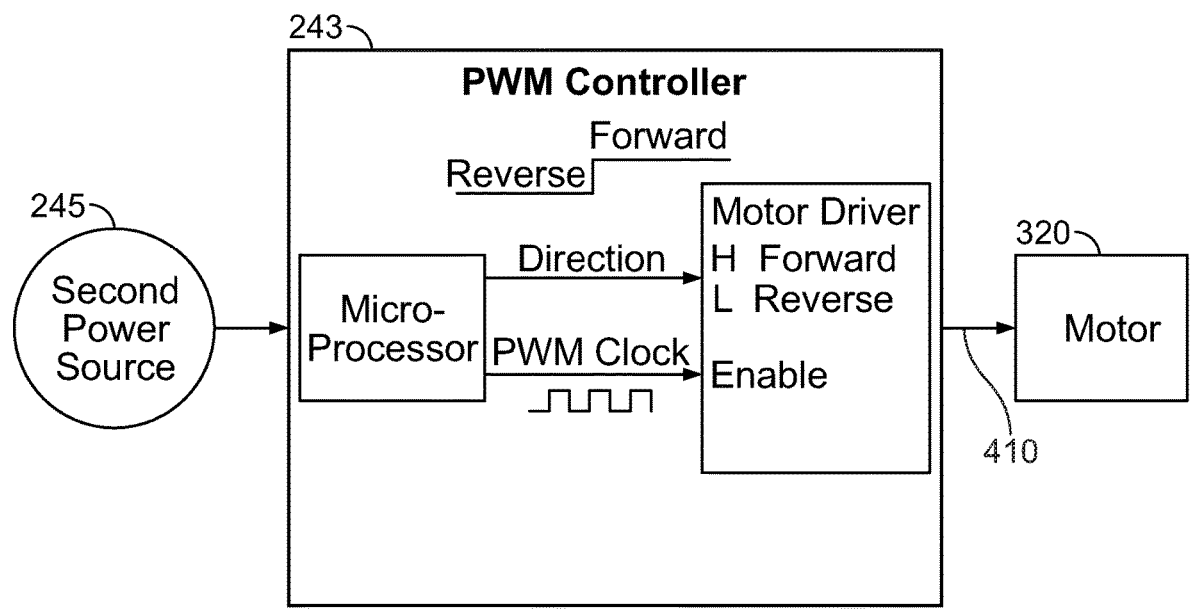
FIG. 24 is a depiction of how a PWM Controller supplies power to the drive system.

Referring to FIG. 24, some embodiments of the infusion pump system 10 can include a pulse width modulation (PWM) controller 243, described in more detail below, for regulating the power to the drive system 300. For example, the drive system 300 can define an energy requirement profile to perform a medicine dispensing operation (e.g., a torque profile). The PWM controller 243 can supply pulses of energy (voltage), of varying widths, to provide an energy profile that correlates to an energy requirement profile (e.g., a torque profile) of the drive system 300. As such, the electrical power drawn from the battery 245 to activate the drive system 300 can be regulated by the PWM controller 243 so as to avoid delivery of substantially more power than is necessary.

In one example, the energy requirement profile can be developed to optimize a plurality of variables, such as power consumption, gear RPM, and the like. The PMW controller 243 can be configured to provide a pattern of voltage pulses from the second power source 245 (e.g., the lithium polymer battery) to the drive system 300. As described in more detail below in connection with FIG. 28, this pattern of voltage pulses controlled by the PWM controller 243 can be correlated to the energy requirement profile (e.g., the torque profile) of the drive system 300. In some embodiments, the torque profile can be developed to maintain the motor 320 at a substantially constant rate of rotation, in spite of changing torque demands on the motor 320 (e.g., from the drive system 300). Maintaining the motor 320 at a substantially constant rate of rotation can have the advantageous qualities of reducing power consumption, reducing vibration, increasing the life of the motor 320, or a combination thereof.

Still referring to FIG. 24, the controller device 200 can house the PWM controller 243 so that it is electrically connected to the second power source 245. The PWM controller 243 can deliver regulated pulses of voltage (e.g., at the voltage supplied by the second power source 245) to the motor 320 of the drive system 300 (FIGS. 17-23). In some embodiments, the motor 320 itself can serve as a passive filter, effectively smoothing out the voltage pulses from the PWM controller 243, without the need for further passive filtering. In alternative embodiments, one or more passive filtering elements can be added to smooth out the pulses from the PWM controller 243.

Figure 25:
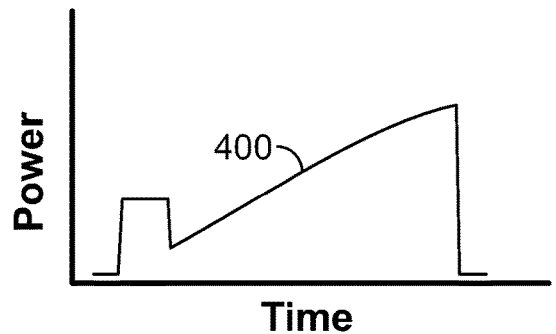
FIG. 25 is a graph depicting an example of a power requirement profile for a drive system.
Figure 26A:
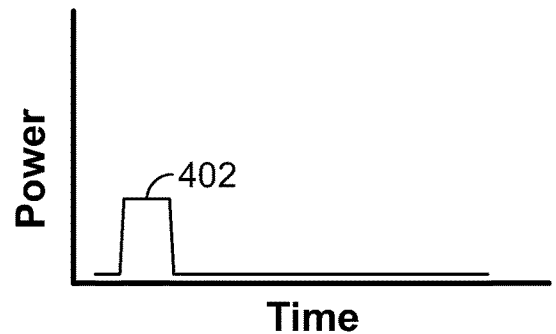
FIG. 26A-26D are graphs depicting theoretical power requirements for a drive system in accordance with some embodiments.
Figure 26B:
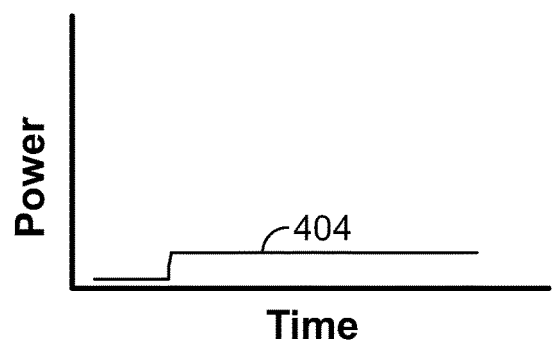
Figure 26C:
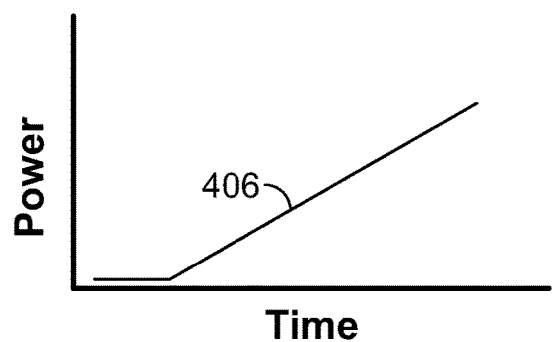
Figure 26D:
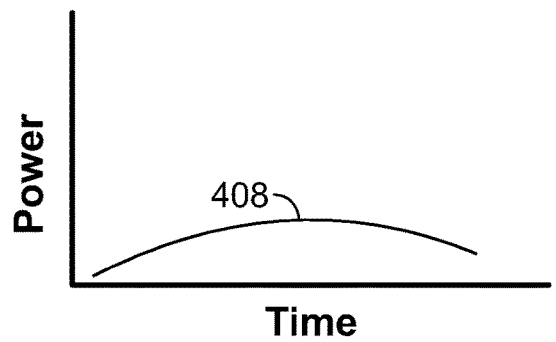

FIG. 25 depicts an example of an optimized torque curve 400 for the drive system 300. This torque curve can represent the torque that is estimated to maintain a constant RPM of the motor 320 when rotating in a first rotational direction that advances the pusher arm 325 to push against the pawl member 335 (refer to FIG. 22). Such movement of the pusher arm 325 can cause a pushing force 327 to overcome the bias of the spring device 350 and can adjust the pawl member 335 toward the reset position. This torque curve 400 can be a sum of, for example, the torque curve 402 associated with initial motor 320 startup (refer to FIG. 26A), the torque curve 404 associated with the no load torque of the motor 320 (the torque required to turn the unladen motor) as depicted in FIG. 26B, the torque curve 406 associated with the torque required to elongate the spring device 350 (refer to FIG. 26C), and/or the torque curve 408 depicted in FIG. 26D that is associated with the mechanical advantage that is achieved due to the connection of the pusher arm 325 to a gear (e.g., the spur gear 325c). While the torque curve 400 here is described as a sum of other torque curves, the torque curve 400 could be determined from empirical data, for example by testing one or more pump devices 100 to determine the actual torque at any given time in a pump cycle required to keep the rate of rotation of the motor 320 substantially constant.

Different pump devices 100 can have different energy requirement profiles (e.g., different torque curves). For example, some pump devices 100 can be actuated by advancing a screw in one direction, which would have a different energy requirement profile than the pump device 300 shown in FIGS. 17-23. In some embodiments, a tachometer can be used to determine an optimum PWM profile for a particular pump device. In embodiments having a brush DC motor, motor commutation can be used as a tachometer surrogate. With a brushless motor the commutation signals are already in digital form and these digital signals can be used as a tachometer signal by measuring their frequency and/or period. It may also be possible to use the actuation period of the drive (interval between limit switch actuations) to provide feedback to the PWM controller to optimize the profile. For example, a PWM profile that provides more power than necessary will result in a faster actuation time, while a PWM profile that fails to provide the optimal amount of power can result in a sluggish actuation or even fail to start the actuation process.

Figure 27:
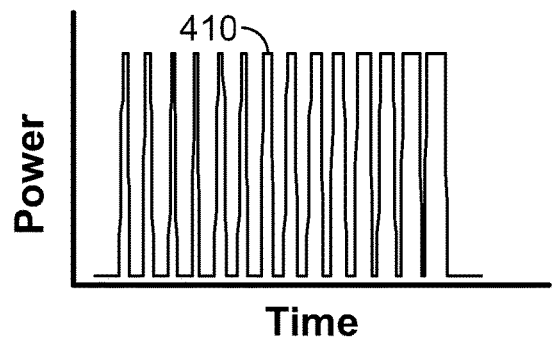
FIG. 27 is a graph depicting a pulse width modulation torque curve in accordance with some embodiments.
Figure 28:
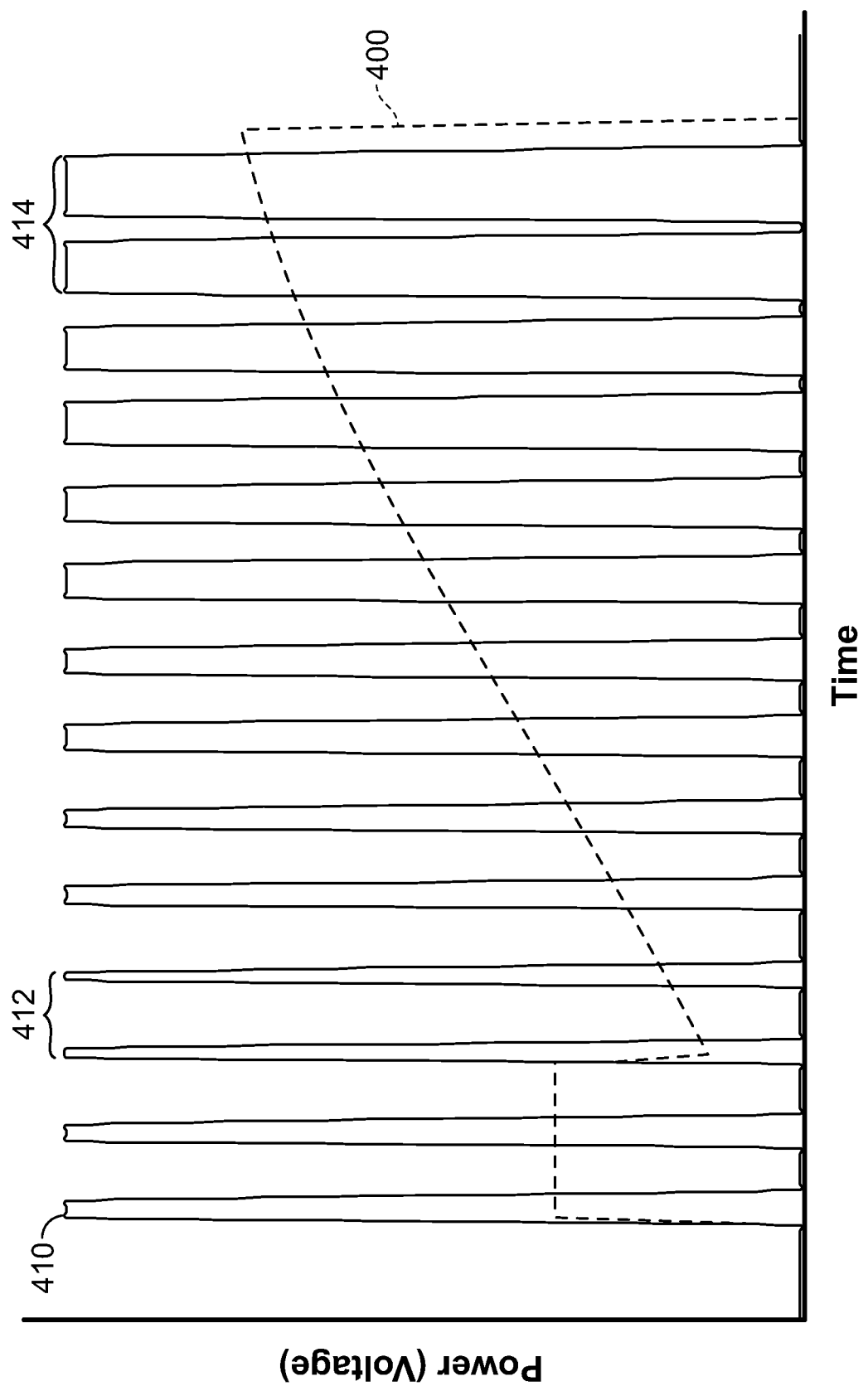
FIG. 28 is a graph depicting a continuous torque curve superimposed on the pulse width modulation torque curve of FIG. 27.

In some embodiments of the infusion pump system 10, the controller device 200 can supply a variable voltage to the motor 320 to achieve a pre-determined torque curve (e.g., the continuous torque curve 400 shown in FIG. 25) using a digital-to-analog (D/A) converter and a power amplifier. In other embodiments, the system 10 can use a series of pulses, all at the full output voltage (e.g., a PWM system) to simulate a continuous torque curve (e.g., torque curve 400) without the need for a D/A converter or power amplifier and without the power loss associated with these components. One exemplary series of PWM pulses is depicted by a PWM torque curve 410 in FIG. 27. Referring to FIG. 28, the continuous torque curve 400 has been superimposed on the PWM torque curve 410. When the torque demands on the motor 320 are low, the width of the delivered pulses is decreased (as in pulses 412). As the torque demands on the motor increase, the width of the delivered pulses is increased (as in pulses 414).

Figure 29A:
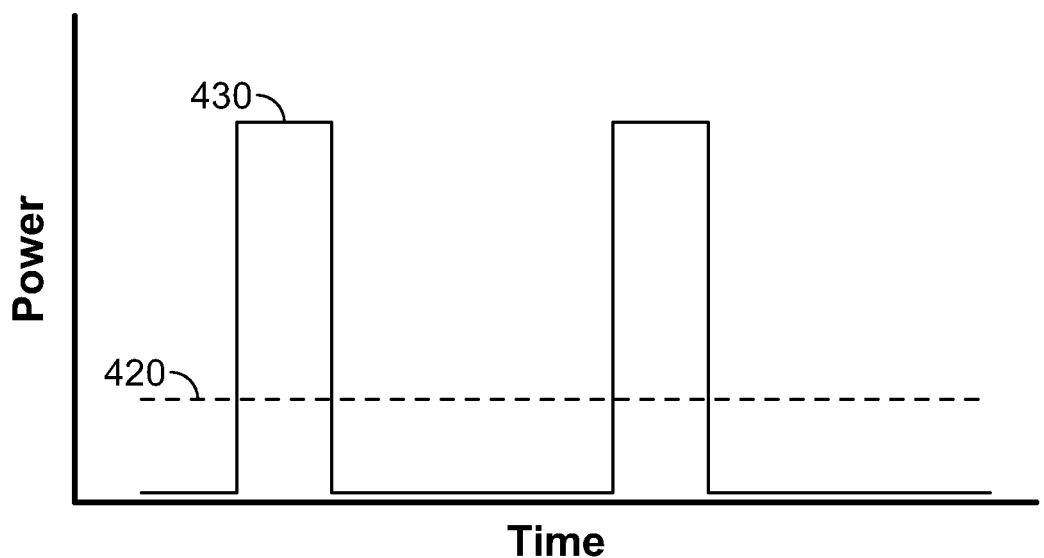
FIGS. 29A and 29B are graphs depicting pulse width modulation torque curves in accordance with some embodiments.
Figure 29B:
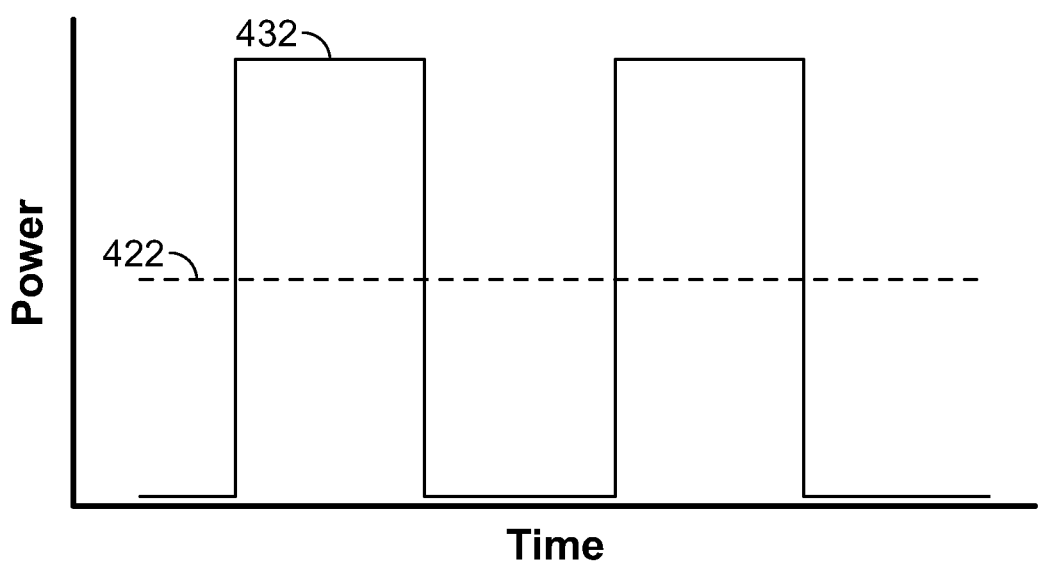

Referring to FIG. 29A-B, a PWM system can work by supplying intermittent, full-voltage, pulses of energy to supply a given amount of energy to a device (e.g., the motor 320) during a period of time. For example, an exemplary motor can be capable of delivering 8 milliNewton*meters with a supply voltage of 4V at 1000 RPM. If, when under load, 2 milliNewton*meters is required to maintain the motor at 1000 RPM for 1 millisecond (as depicted by a continuous torque curve 420 in FIG. 29A), an attached 4 volt system could be "stepped down" using a D/A converter and power amplifier to a voltage (e.g., 1 volt) that supplies a constant 2 mN*m of torque, or 2 mWatts of power, during that 1 msec period, thus delivering a total of 2 microjoules of energy during the 1 msec period. Alternatively, as depicted by a PWM torque curve 430, the attached power source (4V) could be pulsed at a 25% duty cycle (e.g., two 0.125 msec pulses each followed by a 0.375 msec pause during the 1 msec period of time) yielding the same energy output (2 microjoules) during the one millisecond period (2*0.125 msec*8 mN*m). Referring to FIG. 29B, if the same exemplary motor, (one capable of delivering 8 milliNewton*meters with a supply voltage of 4V at 1000 RPM) is required to provide, under load, 4 mN*m during a 1 millisecond (msec) period of time to maintain a constant 1000 RPM (as depicted by torque curve 422), an attached 4 volt system could be "stepped down" using a D/A converter and power amplifier to a voltage (e.g., 2V) to supply a constant 4 mW during that 1 msec period yielding total a total energy of 4 microjoules (4 mW*1 msec). Alternatively, as depicted by a PWM torque curve 432 in FIG. 29B, the attached power source could be pulsed at a 50% duty cycle (e.g., two 0.250 msec pulses each followed by a 0.250 msec pause during the 1 msec period of time) yielding the same energy output (4 microjoules) during the one millisecond period (4*0.125 msec*8 mN*m).

Figure 30A:
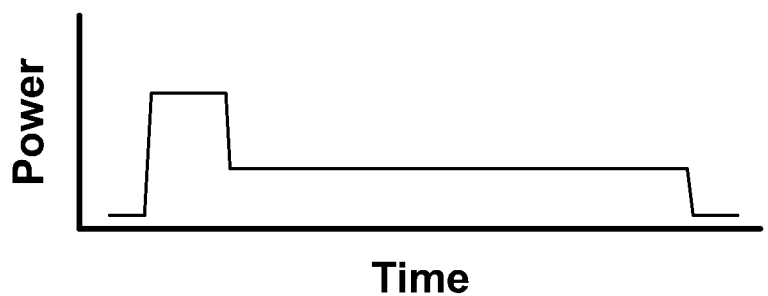
FIGS. 30A, 30B, and 30C are graphs depicting torque curves in accordance with some embodiments.
Figure 30B:
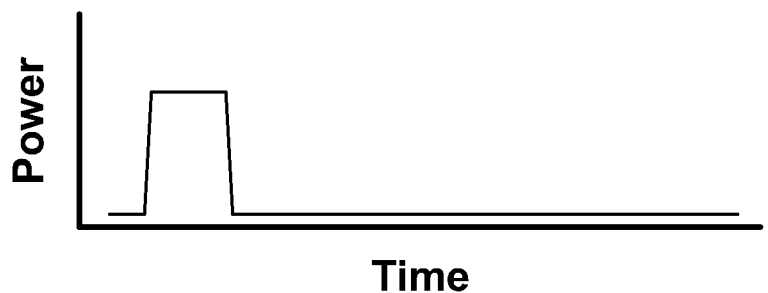
Figure 30C:
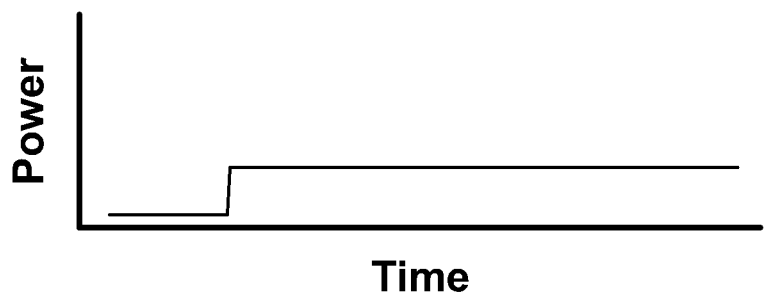

Referring to FIG. 30A, the drive system 300 can have a torque curve 440 that represents the torque that is required, in some embodiments, to maintain a constant RPM of the motor 320 when rotating in a second rotational direction that retracts the pusher arm 325 away from the pawl member 335. Unlike the first rotational direction, when the motor 320 is rotating in the second rotational direction, no force is applied from the spring device 357 to the motor 320. The torque curve for the second rotational direction can be sum of, for example, the torque curve 442 associated with initial startup of the motor 320 (refer to FIG. 30B), and the no-load torque curve 444 of the motor 320 (refer to FIG. 30C). Embodiments of the system 10 that employ a technique for limiting the torque supplied by the motor 320 have the advantage of controlling the RPM of the motor 320, thus conserving energy and reducing vibration associated with over-revving of the motor 320.

Figure 31:
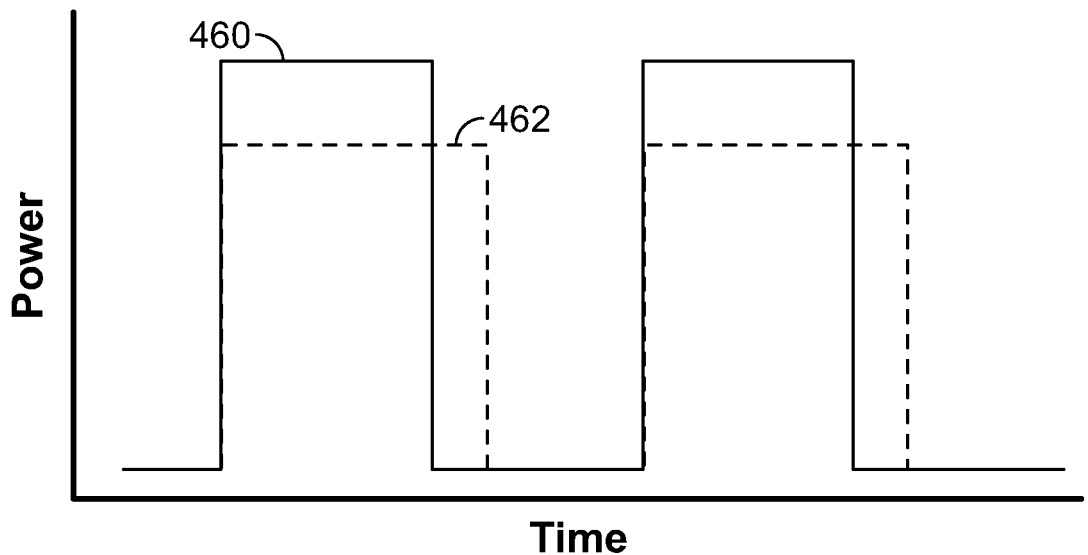
FIG. 31 is a graph depicting an adjustment of pulse widths for changes in voltage output.

In some embodiments of the system 10, the voltage received by the drive system 300 from the second power source 245 can vary due to, for example, the charge remaining in the second power source 245. Referring to the previous example associated with FIG. 29, the pulse widths were determined based on a constant torque output from the power source 245 (e.g., the torque supplied by a 4V input power). However, as the output voltage of the second power source 245 rises and falls, these pulse widths can be adjusted to supply the necessary torque. In one embodiment, a scalar multiple can be applied to the duration of the pulse width to correct for increased or decreased voltage. For example, if the sampled supply voltage to the motor 320 is 3.2 V, instead of the 4V rated output voltage, a scalar multiplier (e.g., 1.25) can be applied to the pulse width to correct for the change in voltage. In some embodiments, a scalar multiplier can be calculated by the controller device 200. Referring to FIG. 31, pulse 450 is an exemplary voltage pulse with a pulse width 452 of 0.20 msec and may have been determined based on an input voltage of 4V. If the input voltage falls to 3.2V, the amount of energy imparted in the pulse is less than if the input voltage was 4V. This imparted energy can be increased by increasing the duration of the pulse 450 (e.g., multiplying the pulse width by a scalar such as 1.25). In this example, the modified pulse 460 has a pulse width 462 of 0.25 msec. In some embodiments, the controller and/or the pump device 100 can store a series of tables in memory for converting between a detected voltage output and an adjustment to the pulse duration (pulse widths) and/or pulse frequency. For example, a detected voltage output of between 3.4 V and 3.5 V can result in the use of a particular table defining a particular PWM pattern for voltage outputs in that range or a particular scalar multiplier adjustment to another PWM pattern stored in memory. The use of tables for particular voltage outputs can reduce the number of computations needed to adjust the PWM pattern for changes in voltage output.

In the preceding embodiments of the PWM system, the voltage of the pulses remained constant, while the width of the pulses were adjusted to maintain the motor 320 at a constant RPM. It should be clear to one skilled in the art that other embodiments of the pulse width modulation system could employ other methods. In one alternate example, the pulse widths could be kept constant, while the pauses in between the pulses could be increased or decreased to simulate a pre-determined torque curve. In additional embodiments, the RPM of the motor 320 could be monitored and the pulse widths could be adjusted based on the RPM of the motor 320.

Figure 32:
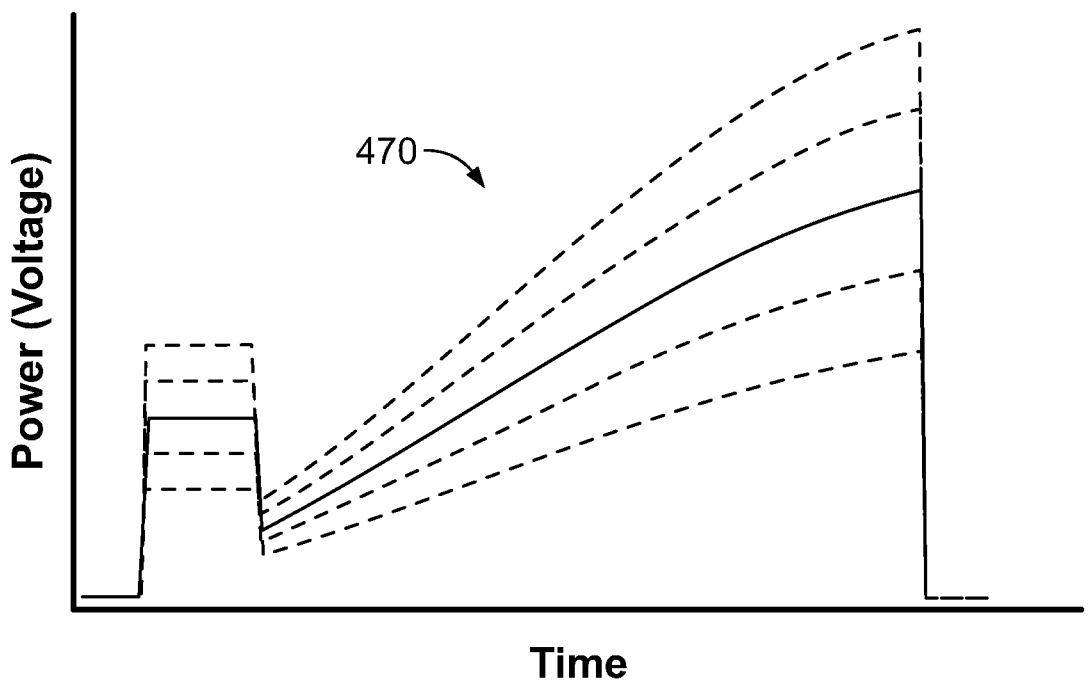
FIG. 32 is a graph depicting an adjustment to the power adjusted torque curves in accordance with some embodiments.

In some embodiments, the controller device 200 can detect a time period for the drive system to complete a medicine dispensing operation and adjust the delivered energy profile to meet the energy requirement profile needed for the drive system. For example, a PWM profile that provides more energy than required can result in a more rapid actuation of the pump device. If the controller device 200 detects that the drive system completed the medicine dispensing operation in less time than a predetermined actuation time, then the controller device 200 can downwardly adjust the delivered energy profile. If the actuation takes more time than a predetermined actuation time, the controller device 200 can upwardly adjust the delivered energy profile. For example a delivered energy profile 470, as shown in FIG. 32, can be upwardly and downwardly adjusted to further optimize the actuation of the drive system. In some embodiments, the controller device 200 can store the delivered energy profile as an adjusted energy requirement profile for the pump. For example, an energy requirement profile for a pump device can be stored in the memory device 318 in the pump device. In cases where the controller device 200 adjusts the delivered energy profile to meet the energy requirement profile needed for the drive system, the controller device 200 can update the energy requirement profile stored on the memory device 318 for subsequent medicine dispensing operations. In some embodiments, the controller device 200 can also detect whether the actuation of the pump actually begins and upwardly adjust the delivered energy profile if the pump fails to start.

A number of embodiments have been described. Nevertheless, it will be understood that various modifications may be made without departing from the spirit and scope of this disclosure. Accordingly, other embodiments are within the scope of the following claims.

What is claimed is:

1. A method of administering medicinal fluid to a patient, the method comprising:
    performing a first medicine dispensing operation by supplying a first pattern of multiple electrical pulses from an energy source to a drive system of a pump device to activate the drive system during a predetermined actuation time;
    determining that the drive system completed the first medicine dispensing operation in less time or more time than the predetermined actuation time;
    in response to determining that the drive system completed the first medicine dispensing operation in less time or more time than the predetermined actuation time, determining a width or frequency for a second pattern of multiple electrical pulses to be supplied as part of a second medicine dispensing operation, wherein the width or frequency for the second pattern of multiple electrical pulses is different than a width or frequency for the first pattern of multiple electrical pulses; and
    performing the second medicine dispensing operation by supplying the second pattern of multiple electrical pulses from the energy source to the drive system according to the determined width or frequency to activate the drive system.

2. The method of claim 1, wherein the first pattern of multiple electrical pulses during the predetermined actuation time corresponds to an incremental dispensing from a series of incremental dispensings of the medicinal fluid.

3. The method of claim 1, wherein the pump device comprises a disposable and non-reusable instrument that houses the energy source.

4. The method of claim 1, wherein the first pattern of multiple electrical pulses is correlated to an energy requirement profile defined by the drive system, and wherein one or more components of the drive system are actuated in response to the delivery of the first pattern of multiple electrical pulses so as to dispense the medicinal fluid from the pump device.

5. The method of claim 4, further comprising:
    determining a voltage of the energy source;
    determining another width or frequency for a third pattern of multiple electrical pulses to be supplied as part of a third medicine dispensing operation, wherein the another width or frequency for the third pattern of multiple electrical pulses is determined at least in part based on the determined voltage of the energy source, and wherein the another width or frequency for the third pattern of multiple electrical pulses is different than the width or frequency for the second pattern of multiple electrical pulses; and
    performing the third medicine dispensing operation by supplying the third pattern of multiple electrical pulses from the energy source to the drive system according to the determined another width or frequency to activate the drive system.

6. The method of claim 4, further comprising:
    detecting a time interval for the drive system to complete the second medicine dispensing operation;
    adjusting the energy requirement profile defined by the drive system based on the detected time interval and a predetermined actuation time for the second medicine dispensing operation; and
    delivering a third pattern of electrical pulses from the energy source to the drive system of the pump device that correlates to the adjusted energy requirement profile defined by the drive system.

7. The method of claim 6, further comprising storing the adjusted energy requirement profile in computer-readable memory in the pump device.

8. The method of claim 1, wherein the drive system comprises a limit switch, and wherein determining that the drive system completed the first medicine dispensing operation in less time or more time than the predetermined actuation time comprises determining the predetermined actuation time based at least in part on one or more limit switch actuations.

9. The method of claim 1, wherein supplied electrical energy for each of the first and second medicine dispensing operations includes an initial period of higher energy supply to overcome static forces of the drive system followed by a second period of lower energy.

10. The method of claim 1, wherein the energy source comprises a rechargeable battery, the method further comprising:
    charging the rechargeable battery with energy from a replaceable battery to maintain the rechargeable battery at a charge level greater than a threshold charge level when the replaceable battery is in a non-depleted state.

11. The method of claim 10, further comprising:
    determining a voltage of the rechargeable battery;
    determining another width or frequency for a third pattern of multiple electrical pulses to be supplied as part of a third medicine dispensing operation, wherein the another width or frequency for the third pattern of multiple electrical pulses is determined at least in part based on the determined voltage of the rechargeable battery, and wherein the another width or frequency for the third pattern of multiple electrical pulses is different than the width or frequency for the second pattern of multiple electrical pulses; and
    performing the third medicine dispensing operation by supplying the third pattern of multiple electrical pulses from the rechargeable battery to the drive system according to the determined another width or frequency to activate the drive system.

12. The method of claim 10, further comprising:
    outputting a user alert indicative of a remaining power supply based at least partially on the threshold charge level when the replaceable battery is in a depleted state or disconnected from electrical communication with the rechargeable energy source.

13. The method of 12, wherein the user alert indicative of the remaining power supply indicates an estimated amount of medicine dispensing time remaining.

14. The method of 13, further comprising detecting a rate of use of the drive system and estimating the estimated amount of medicine dispensing time remaining based on the rate of use of the drive system and the threshold charge level.

15. A wearable infusion pump system, comprising:
a pump device including a drive system to dispense medicine from the pump device;
an energy source to deliver electrical energy to the drive system to initiate actuations of the drive system to perform a medicine dispensing operation;
control circuitry to initiate the medicine dispensing operation by supplying the electrical energy to the drive system;
memory storing executable instructions that, when executed by the control circuitry, cause the wearable infusion pump system to perform operations comprising:
performing a first medicine dispensing operation by supplying a first pattern of multiple electrical pulses from the energy source to the drive system of the pump device to activate the drive system during a predetermined actuation time;
determining that the drive system completed the first medicine dispensing operation in less time or more time than the predetermined actuation time;
in response to determining that the drive system completed the first medicine dispensing operation in less time or more time than the predetermined actuation time, determining a width or frequency for a second pattern of multiple electrical pulses to be supplied as part of a second medicine dispensing operation, wherein the width or frequency for the second pattern of multiple electrical pulses is different than a width or frequency for the first pattern of multiple electrical pulses; and
performing the second medicine dispensing operation by supplying the second pattern of multiple electrical pulses from the energy source to the drive system according to the determined width or frequency to activate the drive system.

16. The infusion pump system of claim 15, wherein the first pattern of multiple electrical pulses is correlated to an energy requirement profile defined by the drive system, and wherein one or more components of the drive system are actuated in response to the delivery of the first pattern of multiple electrical pulses so as to dispense the medicine fluid from the pump device.

17. The infusion pump system of claim 16, the operations further comprising:
detecting a time interval for the drive system to complete the second medicine dispensing operation;
adjusting the energy requirement profile defined by the drive system based on the detected time interval and a predetermined actuation time for the second medicine dispensing operation; and
delivering a third pattern of electrical pulses from the energy source to the drive system of the pump device that correlates to the adjusted energy requirement profile defined by the drive system.

18. The infusion pump system of claim 15, the operations further comprising:
determining a voltage of the energy source;
determining another width or frequency for a third pattern of multiple electrical pulses to be supplied as part of a third medicine dispensing operation, wherein the another width or frequency for the third pattern of multiple electrical pulses is determined at least in part based on the determined voltage of the energy source, and wherein the another width or frequency for the third pattern of multiple electrical pulses is different than the width or frequency for the second pattern of multiple electrical pulses; and
performing the third medicine dispensing operation by supplying the third pattern of multiple electrical pulses from the energy source to the drive system according to the determined another width or frequency to activate the drive system.

19. The infusion pump system of claim 15, wherein the drive system comprises a limit switch, and wherein determining that the drive system completed the first medicine dispensing operation in less time or more time than the predetermined actuation time comprises determining the predetermined actuation time based at least in part on one or more limit switch actuations.

20. The infusion pump system of claim 15, wherein supplied electrical energy for each of the first and second medicine dispensing operations includes an initial period of higher energy supply to overcome static forces of the drive system followed by a second period of lower energy.

* * * * *